(12) United States Patent
Garrison et al.

(10) Patent No.: US 7,628,791 B2
(45) Date of Patent: Dec. 8, 2009

(54) SINGLE ACTION TISSUE SEALER

(75) Inventors: David M. Garrison, Longmont, CO (US); Paul Hermes, Guilford, CT (US); Sean Dycus, Broomfield, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 522 days.

(21) Appl. No.: 11/207,956

(22) Filed: Aug. 19, 2005

(65) Prior Publication Data
US 2007/0043352 A1    Feb. 22, 2007

(51) Int. Cl.
A61B 18/14    (2006.01)
A61B 17/32    (2006.01)

(52) U.S. Cl. .................................. 606/51; 606/171
(58) Field of Classification Search .................. 606/45, 606/48, 51, 52, 171
See application file for complete search history.

(56) References Cited

U.S. PATENT DOCUMENTS

| | | | |
|---|---|---|---|
| 371,664 | A | 10/1887 | Brannan et al. |
| 702,472 | A | 6/1902 | Pignolet |
| 728,883 | A | 5/1903 | Downes |
| 1,586,645 | A | 6/1926 | Bierman |
| 1,813,902 | A | 7/1931 | Bovie |
| 2,002,594 | A | 5/1935 | Wappler et al. |
| 2,011,169 | A | 8/1935 | Wappler |
| 2,031,682 | A | 2/1936 | Wappler et al. |
| 2,176,479 | A | 10/1939 | Willis |
| 2,279,753 | A | 4/1942 | Knopp |
| 2,305,156 | A | 12/1942 | Grubel |
| 2,632,661 | A | 3/1953 | Cristofv |
| 2,668,538 | A | 2/1954 | Baker |
| 2,796,065 | A | 6/1957 | Kapp |
| 3,459,187 | A | 8/1969 | Pallotta |
| 3,643,663 | A | 2/1972 | Sutter |

(Continued)

FOREIGN PATENT DOCUMENTS

CA    2104423    2/1994

(Continued)

OTHER PUBLICATIONS

Sigel et al. "The Mechanism of Blood Vessel Closure by High Frequency Electrocoagulation" Surgery Gynecology & Obstetrics, Oct. 1965 pp. 823-831.

(Continued)

*Primary Examiner*—Lee S Cohen

(57) ABSTRACT

An endoscopic bipolar forceps includes a housing and a shaft, the shaft having an end effector assembly at its distal end. The end effector assembly includes two jaw members for grasping tissue therebetween. The jaw members are adapted to connect to an electrosurgical energy source which enable them to conduct energy through the tissue to create a tissue seal. A drive assembly is disposed within the housing which moves the jaw members. A switch is disposed within the housing which activates the electrosurgical energy. A knife assembly is included which is advanceable to cut tissue held between the jaw members. A movable handle is connected to the housing. Continual actuation of the movable handle engages the drive assembly to move the jaw members, engages the switch to activate the electrosurgical energy source to seal the tissue, and advances the knife assembly the cut the tissue disposed between the jaw members.

14 Claims, 16 Drawing Sheets

U.S. PATENT DOCUMENTS

| | | |
|---|---|---|
| 3,651,811 A | 3/1972 | Hildebrandt et al. |
| 3,720,896 A | 3/1973 | Beierlein |
| 3,862,630 A | 1/1975 | Balamuth |
| 3,863,339 A | 2/1975 | Reaney et al. |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,088,134 A | 5/1978 | Mazzariello |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,233,734 A | 11/1980 | Bies |
| 4,300,564 A | 11/1981 | Furihata |
| D263,020 S | 2/1982 | Rau, III |
| 4,370,980 A | 2/1983 | Lottick |
| 4,375,218 A | 3/1983 | DiGeronimo |
| 4,416,276 A | 11/1983 | Newton et al. |
| 4,418,692 A | 12/1983 | Guay |
| 4,452,246 A | 6/1984 | Bader et al. |
| 4,492,231 A | 1/1985 | Auth |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| 4,827,929 A | 5/1989 | Hodge |
| 4,846,171 A | 7/1989 | Kauphusman et al. |
| 4,887,612 A | 12/1989 | Esser et al. |
| 4,938,761 A | 7/1990 | Ensslin |
| 4,985,030 A | 1/1991 | Melzer et al. |
| 5,007,908 A | 4/1991 | Rydell |
| 5,026,370 A | 6/1991 | Lottick |
| 5,035,695 A | 7/1991 | Weber, Jr. et al. |
| 5,084,057 A | 1/1992 | Green et al. |
| 5,099,840 A | 3/1992 | Goble et al. |
| 5,116,332 A | 5/1992 | Lottick |
| 5,147,357 A | 9/1992 | Rose et al. |
| 5,151,102 A | 9/1992 | Xamiyama et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,290,286 A | 3/1994 | Parins |
| 5,304,203 A | 4/1994 | El-Mallawany et al. |
| 5,308,357 A | 5/1994 | Lichtman |
| 5,314,445 A | 5/1994 | Degwitz et al. |
| 5,318,589 A | 6/1994 | Lichtman |
| 5,324,289 A | 6/1994 | Eggers |
| 5,326,806 A | 7/1994 | Yokoshima et al. |
| 5,330,471 A | 7/1994 | Eggers |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,376,089 A | 12/1994 | Smith |
| 5,383,897 A | 1/1995 | Wholey |
| 5,389,098 A | 2/1995 | Tsuruta et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,403,312 A | 4/1995 | Yates et al. |
| 5,411,519 A | 5/1995 | Tovey et al. |
| 5,411,520 A | 5/1995 | Nash et al. |
| 5,413,571 A | 5/1995 | Katsaros et al. |
| 5,415,657 A | 5/1995 | Taymor-Luria |
| 5,422,567 A | 6/1995 | Matsunaga |
| 5,423,810 A | 6/1995 | Goble et al. |
| 5,425,690 A | 6/1995 | Chang |
| 5,425,739 A | 6/1995 | Jessen |
| 5,429,616 A | 7/1995 | Schaffer |
| 5,431,672 A | 7/1995 | Cote et al. |
| 5,431,674 A | 7/1995 | Basile et al. |
| 5,437,292 A | 8/1995 | Kipshidze et al. |
| 5,438,302 A | 8/1995 | Goble |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,451,224 A | 9/1995 | Goble et al. |
| 5,456,684 A | 10/1995 | Schmidt et al. |
| 5,458,598 A | 10/1995 | Feinberg et al. |
| 5,460,629 A | 10/1995 | Shlain et al. |
| 5,462,546 A | 10/1995 | Rydell |
| 5,472,443 A | 12/1995 | Cordis et al. |
| 5,478,351 A | 12/1995 | Meade et al. |
| 5,480,409 A | 1/1996 | Riza |
| 5,484,436 A | 1/1996 | Eggers et al. |
| 5,496,312 A | 3/1996 | Klicek |
| 5,496,317 A | 3/1996 | Goble et al. |
| 5,496,347 A | 3/1996 | Hashiguchi et al. |
| 5,499,997 A | 3/1996 | Sharpe et al. |
| 5,509,922 A | 4/1996 | Aranyi et al. |
| 5,514,134 A | 5/1996 | Rydell et al. |
| 5,527,313 A | 6/1996 | Scott et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,715 A | 7/1996 | Katsaros et al. |

| | | | | | |
|---|---|---|---|---|---|
| 5,542,945 A | 8/1996 | Fritzsch | 5,817,093 A | 10/1998 | Williamson, IV et al. |
| 5,558,671 A | 9/1996 | Yates | 5,820,630 A | 10/1998 | Lind |
| 5,558,672 A | 9/1996 | Edwards et al. | 5,827,271 A | 10/1998 | Buysse et al. |
| 5,562,699 A | 10/1996 | Heimberger et al. | 5,827,279 A | 10/1998 | Hughett et al. |
| 5,569,241 A | 10/1996 | Edwardds | 5,827,281 A | 10/1998 | Levin |
| 5,569,243 A | 10/1996 | Kortenbach et al. | 5,827,323 A | 10/1998 | Klieman et al. |
| 5,571,100 A | 11/1996 | Goble et al. | 5,827,548 A | 10/1998 | Lavallee et al. |
| 5,573,424 A | 11/1996 | Poppe | 5,833,690 A | 11/1998 | Yates et al. |
| 5,573,534 A | 11/1996 | Stone | 5,843,080 A | 12/1998 | Fleenor et al. |
| 5,573,535 A | 11/1996 | Viklund | 5,849,022 A | 12/1998 | Sakashita et al. |
| 5,575,805 A | 11/1996 | Li | 5,853,412 A | 12/1998 | Mayenberger |
| 5,578,052 A | 11/1996 | Koros et al. | 5,860,976 A | 1/1999 | Billings et al. |
| 5,582,611 A | 12/1996 | Tsukagoshi et al. | 5,876,401 A | 3/1999 | Schulze et al. |
| 5,585,896 A | 12/1996 | Yamazaki et al. | 5,882,567 A | 3/1999 | Cavallaro et al. |
| 5,590,570 A | 1/1997 | LeMaire, III et al. | 5,891,141 A | 4/1999 | Rydell |
| 5,601,601 A | 2/1997 | Tal et al. | 5,891,142 A | 4/1999 | Eggers et al. |
| 5,603,711 A | 2/1997 | Parins et al. | 5,893,863 A | 4/1999 | Yoon |
| 5,603,723 A | 2/1997 | Aranyi et al. | 5,893,875 A | 4/1999 | O'Connor et al. |
| 5,611,798 A | 3/1997 | Eggers | 5,893,877 A | 4/1999 | Gampp, Jr. et al. |
| 5,620,453 A | 4/1997 | Nallakrishnan | 5,902,301 A | 5/1999 | Olig |
| 5,624,452 A | 4/1997 | Yates | 5,906,630 A | 5/1999 | Anderhub et al. |
| 5,626,578 A | 5/1997 | Tihon | 5,908,420 A | 6/1999 | Parins et al. |
| 5,626,609 A | 5/1997 | Zvenyatsky et al. | 5,908,432 A | 6/1999 | Pan |
| 5,630,833 A | 5/1997 | Katsaros et al. | 5,911,719 A | 6/1999 | Eggers |
| 5,637,110 A | 6/1997 | Pennybacker et al. | 5,913,874 A | 6/1999 | Berns et al. |
| 5,638,003 A | 6/1997 | Hall | 5,921,984 A | 7/1999 | Sutcu et al. |
| 5,643,294 A | 7/1997 | Tovey et al. | 5,925,043 A | 7/1999 | Kumar et al. |
| 5,647,869 A | 7/1997 | Goble et al. | 5,935,126 A | 8/1999 | Riza |
| 5,647,871 A | 7/1997 | Levine et al. | 5,944,718 A | 8/1999 | Dafforn et al. |
| 5,649,959 A | 7/1997 | Hannam et al. | 5,951,549 A | 9/1999 | Richardson et al. |
| 5,658,281 A | 8/1997 | Heard | 5,954,720 A | 9/1999 | Wilson et al. |
| 5,662,667 A | 9/1997 | Knodel | 5,957,923 A | 9/1999 | Hahnen et al. |
| 5,665,100 A | 9/1997 | Yoon | 5,960,544 A | 10/1999 | Beyers |
| 5,667,526 A | 9/1997 | Levin | 5,961,514 A | 10/1999 | Long et al. |
| 5,674,220 A | 10/1997 | Fox et al. | 5,964,758 A | 10/1999 | Dresden |
| 5,681,282 A | 10/1997 | Eggers et al. | 5,976,132 A | 11/1999 | Morris |
| 5,688,270 A | 11/1997 | Yates et al. | 5,984,939 A | 11/1999 | Yoon |
| 5,693,051 A | 12/1997 | Schulze et al. | 5,989,277 A | 11/1999 | LeMaire, III et al. |
| 5,695,522 A | 12/1997 | LeMaire, III et al. | 5,997,565 A | 12/1999 | Inoue |
| 5,700,261 A | 12/1997 | Brinkerhoff | 6,004,335 A | 12/1999 | Vaitekunas et al. |
| 5,702,390 A | 12/1997 | Austin et al. | 6,010,516 A | 1/2000 | Hulka |
| 5,707,369 A | 1/1998 | Vaitekunas et al. | 6,024,741 A | 2/2000 | Williamson et al. |
| 5,709,680 A | 1/1998 | Yates et al. | 6,024,744 A | 2/2000 | Kese et al. |
| 5,716,366 A | 2/1998 | Yates | 6,030,384 A | 2/2000 | Nezhat |
| 5,720,744 A | 2/1998 | Eggleston et al. | 6,033,399 A | 3/2000 | Gines |
| 5,722,421 A | 3/1998 | Francese et al. | 6,039,733 A | 3/2000 | Buysse et al. |
| 5,725,536 A | 3/1998 | Oberlin et al. | 6,041,679 A | 3/2000 | Slater et al. |
| 5,727,428 A | 3/1998 | LeMaire, III et al. | 6,050,996 A | 4/2000 | Schmaltz et al. |
| 5,735,848 A | 4/1998 | Yates et al. | 6,053,914 A | 4/2000 | Eggers et al. |
| 5,743,906 A | 4/1998 | Parins et al. | 6,053,933 A | 4/2000 | Balazs et al. |
| 5,755,717 A | 5/1998 | Yates et al. | D424,694 S | 5/2000 | Tetzlaff et al. |
| 5,766,130 A | 6/1998 | Selmonosky | D425,201 S | 5/2000 | Tetzlaff et al. |
| 5,766,166 A | 6/1998 | Hooven | 6,059,782 A | 5/2000 | Novak et al. |
| 5,766,170 A | 6/1998 | Eggers | 6,074,386 A | 6/2000 | Goble et al. |
| 5,769,849 A | 6/1998 | Eggers | RE36,795 E | 7/2000 | Rydell |
| 5,772,655 A | 6/1998 | Bauer et al. | 6,083,223 A | 7/2000 | Baker |
| 5,772,670 A | 6/1998 | Brosa | 6,086,586 A | 7/2000 | Hooven |
| 5,776,128 A | 7/1998 | Eggers | 6,090,107 A | 7/2000 | Borgmeier et al. |
| 5,776,130 A | 7/1998 | Buysse et al. | 6,096,037 A | 8/2000 | Mulier et al. |
| 5,779,701 A | 7/1998 | McBrayer et al. | 6,099,550 A | 8/2000 | Yoon |
| H1745 H | 8/1998 | Paraschac | 6,102,909 A | 8/2000 | Chen et al. |
| 5,792,137 A | 8/1998 | Carr et al. | 6,110,171 A | 8/2000 | Rydell |
| 5,792,177 A | 8/1998 | Kaseda | 6,113,596 A | 9/2000 | Hooven et al. |
| 5,797,927 A | 8/1998 | Yoon | 6,113,598 A | 9/2000 | Baker |
| 5,797,938 A | 8/1998 | Paraschac et al. | 6,117,158 A | 9/2000 | Measamer et al. |
| 5,797,941 A | 8/1998 | Schulze et al. | 6,123,701 A | 9/2000 | Nezhat |
| 5,797,958 A | 8/1998 | Yoon | 6,126,658 A | 10/2000 | Baker |
| 5,800,449 A | 9/1998 | Wales | 6,152,923 A | 11/2000 | Ryan |
| 5,807,393 A | 9/1998 | Williamson, IV et al. | 6,162,220 A | 12/2000 | Nezhat |
| 5,810,808 A | 9/1998 | Eggers | 6,174,309 B1 | 1/2001 | Wrublewski et al. |
| 5,810,811 A | 9/1998 | Yates et al. | 6,179,834 B1 | 1/2001 | Buysse et al. |
| 5,810,877 A | 9/1998 | Roth et al. | 6,179,837 B1 | 1/2001 | Hooven |
| 5,814,043 A | 9/1998 | Shapeton | 6,183,467 B1 | 2/2001 | Shapeton et al. |

| | | |
|---|---|---|
| 6,187,003 B1 | 2/2001 | Buysse et al. |
| 6,190,386 B1 | 2/2001 | Rydell |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,217,602 B1 | 4/2001 | Redmon |
| 6,221,039 B1 | 4/2001 | Durgin et al. |
| 6,224,593 B1 | 5/2001 | Ryan et al. |
| 6,228,080 B1 | 5/2001 | Gines |
| 6,228,083 B1 | 5/2001 | Lands et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,302,424 B1 | 10/2001 | Gisinger et al. |
| 6,319,451 B1 | 11/2001 | Brune |
| 6,322,561 B1 | 11/2001 | Eggers et al. |
| 6,334,860 B1 | 1/2002 | Dorn |
| 6,334,861 B1 | 1/2002 | Chandler et al. |
| 6,345,532 B1 | 2/2002 | Coudray et al. |
| 6,350,264 B1 | 2/2002 | Hooven |
| 6,352,536 B1 | 3/2002 | Buysse et al. |
| 6,358,249 B1 | 3/2002 | Chen et al. |
| 6,358,268 B1 | 3/2002 | Hunt et al. |
| D457,958 S | 5/2002 | Dycus et al. |
| D457,959 S | 5/2002 | Tetzlaff et al. |
| 6,387,094 B1 * | 5/2002 | Eitenmuller .............. 606/48 |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| 6,419,675 B1 | 7/2002 | Gallo, Sr. |
| 6,425,896 B1 | 7/2002 | Baltschun et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,130 B1 | 10/2002 | Frazier et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,500,176 B1 | 12/2002 | Truckai et al. |
| 6,511,480 B1 | 1/2003 | Tetzlaff et al. |
| 6,514,252 B2 | 2/2003 | Nezhat et al. |
| 6,527,771 B1 | 3/2003 | Weadock et al. |
| 6,558,385 B1 | 5/2003 | McClurken et al. |
| 6,562,037 B2 | 5/2003 | Paton et al. |
| 6,585,735 B1 | 7/2003 | Frazier et al. |
| 6,602,252 B2 | 8/2003 | Mollenauer |
| 6,616,658 B2 | 9/2003 | Ineson |
| 6,616,661 B2 | 9/2003 | Wellman et al. |
| 6,620,161 B2 | 9/2003 | Schulze et al. |
| 6,626,901 B1 | 9/2003 | Treat et al. |
| 6,641,595 B1 | 11/2003 | Moran et al. |
| 6,652,514 B2 | 11/2003 | Ellman et al. |
| 6,652,521 B2 | 11/2003 | Schulze |
| 6,656,177 B2 | 12/2003 | Truckai et al. |
| 6,660,072 B2 | 12/2003 | Chatterjee |
| 6,669,696 B2 | 12/2003 | Bacher et al. |
| 6,676,660 B2 | 1/2004 | Wampler et al. |
| 6,679,882 B1 | 1/2004 | Kornerup |
| 6,682,527 B2 | 1/2004 | Strul |
| 6,682,528 B2 | 1/2004 | Frazier et al. |
| 6,685,724 B1 | 2/2004 | Haluck |
| 6,689,131 B2 | 2/2004 | McClurken |
| 6,692,445 B2 | 2/2004 | Roberts et al. |
| 6,695,840 B2 | 2/2004 | Schulze |
| 6,702,810 B2 | 3/2004 | McClurken et al. |
| 6,726,068 B2 | 4/2004 | Miller |
| 6,726,686 B2 | 4/2004 | Buysse et al. |
| 6,733,498 B2 | 5/2004 | Paton et al. |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,757,977 B2 | 7/2004 | Dambal et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,775,575 B2 | 8/2004 | Bommannan et al. |
| 6,776,780 B2 | 8/2004 | Mulier et al. |
| 6,790,217 B2 | 9/2004 | Schulze et al. |
| 6,796,981 B2 | 9/2004 | Wham et al. |
| D496,997 S | 10/2004 | Dycus et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,887,240 B1 | 5/2005 | Lands et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| 6,942,662 B2 | 9/2005 | Goble et al. |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,977,495 B2 | 12/2005 | Donofrio |
| 6,979,786 B2 | 12/2005 | Aukland et al. |
| 6,994,707 B2 | 2/2006 | Ellman et al. |
| 6,994,709 B2 | 2/2006 | Iida |
| 7,011,657 B2 | 3/2006 | Truckai et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,496 B2 | 5/2006 | Yamauchi |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,112,199 B2 | 9/2006 | Cosmescu |
| D531,311 S | 10/2006 | Guerra et al. |
| 7,115,123 B2 | 10/2006 | Knowlton et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,020 B2 | 11/2006 | Lawes et al. |
| D533,942 S | 12/2006 | Kerr et al. |
| 7,145,757 B2 | 12/2006 | Shea et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| D535,027 S | 1/2007 | James et al. |
| 7,156,842 B2 | 1/2007 | Sartor et al. |
| 7,156,846 B2 | 1/2007 | Dycus et al. |
| 7,160,298 B2 | 1/2007 | Lawes et al. |
| 7,160,299 B2 | 1/2007 | Baily |

| | | |
|---|---|---|
| 7,169,146 B2 | 1/2007 | Truckai et al. |
| 7,179,258 B2 | 2/2007 | Buysse et al. |
| 7,195,631 B2 | 3/2007 | Dumbauld |
| D541,418 S | 4/2007 | Schechter et al. |
| 7,207,990 B2 | 4/2007 | Lands et al. |
| D541,938 S | 5/2007 | Kerr et al |
| 7,223,265 B2 | 5/2007 | Keppel |
| 7,232,440 B2 | 6/2007 | Dumbauld et al. |
| 7,241,288 B2 | 7/2007 | Braun |
| 7,241,296 B2 | 7/2007 | Buysse et al. |
| 7,252,667 B2 | 8/2007 | Moses et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,300,435 B2 | 11/2007 | Wham et al. |
| 7,303,557 B2 | 12/2007 | Wham et al. |
| 7,314,471 B2 | 1/2008 | Holman |
| 7,329,256 B2 | 2/2008 | Johnson et al. |
| 7,329,257 B2 | 2/2008 | Kanehira et al. |
| D564,662 S | 3/2008 | Moses et al. |
| 7,342,754 B2 | 3/2008 | Fitzgerald et al. |
| 7,344,268 B2 | 3/2008 | Jigamian |
| 7,367,976 B2 | 5/2008 | Lawes et al. |
| 2002/0013583 A1 | 1/2002 | Camran et al. |
| 2002/0049442 A1 | 4/2002 | Roberts et al. |
| 2002/0099372 A1 | 7/2002 | Schulze et al. |
| 2002/0107517 A1 | 8/2002 | Witt et al. |
| 2002/0111624 A1 | 8/2002 | Witt et al. |
| 2002/0188294 A1 | 12/2002 | Couture et al. |
| 2003/0014052 A1 | 1/2003 | Buysse et al. |
| 2003/0014053 A1 | 1/2003 | Nguyen et al. |
| 2003/0018331 A1 | 1/2003 | Dycus et al. |
| 2003/0018332 A1 | 1/2003 | Schmaltz et al. |
| 2003/0032956 A1 | 2/2003 | Lands et al. |
| 2003/0055424 A1* | 3/2003 | Ciarrocca .................... 606/51 |
| 2003/0069571 A1 | 4/2003 | Treat et al. |
| 2003/0078578 A1 | 4/2003 | Truckai et al. |
| 2003/0109875 A1 | 6/2003 | Tetzlaff et al. |
| 2003/0114851 A1 | 6/2003 | Truckai et al. |
| 2003/0139741 A1 | 7/2003 | Goble et al. |
| 2003/0139742 A1 | 7/2003 | Wampler et al. |
| 2003/0158549 A1 | 8/2003 | Swanson |
| 2003/0181910 A1 | 9/2003 | Dycus et al. |
| 2003/0199869 A1 | 10/2003 | Johnson et al. |
| 2003/0216732 A1 | 11/2003 | Truckai et al. |
| 2003/0220637 A1 | 11/2003 | Truckai et al. |
| 2003/0229344 A1 | 12/2003 | Dycus et al. |
| 2004/0030330 A1 | 2/2004 | Brassell et al. |
| 2004/0030332 A1 | 2/2004 | Knowlton et al. |
| 2004/0049185 A1 | 3/2004 | Latterell et al. |
| 2004/0064151 A1 | 4/2004 | Mollenauer |
| 2004/0078035 A1 | 4/2004 | Kanehira et al. |
| 2004/0082952 A1 | 4/2004 | Dycus et al. |
| 2004/0087943 A1 | 5/2004 | Dycus et al. |
| 2004/0115296 A1 | 6/2004 | Duffin |
| 2004/0116924 A1 | 6/2004 | Dycus et al. |
| 2004/0116979 A1 | 6/2004 | Truckai et al. |
| 2004/0122423 A1 | 6/2004 | Dycus et al. |
| 2004/0143263 A1 | 7/2004 | Schechter et al. |
| 2004/0147925 A1 | 7/2004 | Buysse et al. |
| 2004/0162557 A1 | 8/2004 | Tetzlaff et al. |
| 2004/0176762 A1 | 9/2004 | Lawes et al. |
| 2004/0193153 A1 | 9/2004 | Sarter et al. |
| 2004/0225288 A1 | 11/2004 | Buysse et al. |
| 2004/0230189 A1 | 11/2004 | Keppel |
| 2004/0236325 A1 | 11/2004 | Tetzlaff et al. |
| 2004/0236326 A1 | 11/2004 | Schulze et al. |
| 2004/0243125 A1 | 12/2004 | Dycus et al. |
| 2004/0249371 A1 | 12/2004 | Dycus et al. |
| 2004/0249374 A1 | 12/2004 | Tetzlaff et al. |
| 2004/0250419 A1 | 12/2004 | Sremcich et al. |
| 2004/0254573 A1 | 12/2004 | Dycus et al. |
| 2004/0260281 A1 | 12/2004 | Baxter, III et al. |
| 2005/0004564 A1 | 1/2005 | Wham et al. |
| 2005/0004568 A1 | 1/2005 | Lawes et al. |
| 2005/0004570 A1 | 1/2005 | Chapman et al. |
| 2005/0021025 A1 | 1/2005 | Buysse et al. |
| 2005/0021026 A1 | 1/2005 | Baily |
| 2005/0021027 A1 | 1/2005 | Shields et al. |
| 2005/0033278 A1 | 2/2005 | McClurken et al. |
| 2005/0096645 A1 | 5/2005 | Wellman et al. |
| 2005/0101951 A1 | 5/2005 | Wham et al. |
| 2005/0101952 A1 | 5/2005 | Lands et al. |
| 2005/0107784 A1 | 5/2005 | Moses et al. |
| 2005/0107785 A1 | 5/2005 | Dycus et al. |
| 2005/0113818 A1 | 5/2005 | Sartor et al. |
| 2005/0113819 A1 | 5/2005 | Wham et al. |
| 2005/0113826 A1 | 5/2005 | Johnson et al. |
| 2005/0113827 A1 | 5/2005 | Dumbauld et al. |
| 2005/0113828 A1 | 5/2005 | Shields et al. |
| 2005/0119655 A1 | 6/2005 | Moses et al. |
| 2005/0149017 A1 | 7/2005 | Dycus |
| 2005/0149151 A1 | 7/2005 | Orszulak et al. |
| 2005/0187547 A1 | 8/2005 | Sugi |
| 2005/0197659 A1 | 9/2005 | Bahney |
| 2005/0203504 A1 | 9/2005 | Wham et al. |
| 2005/0240179 A1 | 10/2005 | Buysse et al. |
| 2006/0052778 A1 | 3/2006 | Chapman et al. |
| 2006/0064085 A1 | 3/2006 | Schechter et al. |
| 2006/0074417 A1 | 4/2006 | Cunningham et al. |
| 2006/0079888 A1 | 4/2006 | Mulier et al. |
| 2006/0079890 A1 | 4/2006 | Guerra |
| 2006/0079891 A1 | 4/2006 | Arts et al. |
| 2006/0116675 A1 | 6/2006 | McClurken et al. |
| 2006/0129146 A1 | 6/2006 | Dycus et al. |
| 2006/0161150 A1 | 7/2006 | Keppel |
| 2006/0167450 A1 | 7/2006 | Johnson et al. |
| 2006/0167452 A1 | 7/2006 | Moses et al. |
| 2006/0173452 A1 | 8/2006 | Buysse et al. |
| 2006/0189980 A1 | 8/2006 | Johnson et al. |
| 2006/0189981 A1 | 8/2006 | Dycus et al. |
| 2006/0190035 A1 | 8/2006 | Hushka et al. |
| 2006/0217709 A1 | 9/2006 | Couture et al. |
| 2006/0224158 A1 | 10/2006 | Odom et al. |
| 2006/0259036 A1 | 11/2006 | Tetzlaf et al. |
| 2006/0264922 A1 | 11/2006 | Sartor et al. |
| 2006/0264931 A1 | 11/2006 | Chapman et al. |
| 2006/0271038 A1 | 11/2006 | Johnson et al. |
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0043352 A1 | 2/2007 | Garrison et al. |
| 2007/0043353 A1 | 2/2007 | Dycus et al. |
| 2007/0055231 A1 | 3/2007 | Dycus et al. |
| 2007/0060919 A1 | 3/2007 | Isaacson et al. |
| 2007/0062017 A1 | 3/2007 | Dycus et al. |
| 2007/0074807 A1 | 4/2007 | Guerra |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0106295 A1 | 5/2007 | Garrison et al. |
| 2007/0106297 A1 | 5/2007 | Dumbauld et al. |
| 2007/0118111 A1 | 5/2007 | Weinberg |
| 2007/0118115 A1 | 5/2007 | Artale et al. |
| 2007/0142833 A1 | 6/2007 | Dycus et al. |
| 2007/0142834 A1 | 6/2007 | Dumbauld |
| 2007/0156139 A1 | 7/2007 | Schechter et al. |
| 2007/0156140 A1 | 7/2007 | Baily |
| 2007/0173811 A1 | 7/2007 | Couture et al. |
| 2007/0173814 A1 | 7/2007 | Hixson et al. |
| 2007/0179499 A1 | 8/2007 | Garrison |
| 2007/0203485 A1 | 8/2007 | Keppel |
| 2007/0213706 A1 | 9/2007 | Dumbauld et al. |

| | | | | | | |
|---|---|---|---|---|---|---|
| 2007/0213707 A1 | 9/2007 | Dumbauld et al. | | GB | 2213416 | 8/1989 |
| 2007/0213708 A1 | 9/2007 | Dumbauld et al. | | JP | 501068 | 9/1984 |
| 2007/0213712 A1 | 9/2007 | Buysse et al. | | JP | 502328 | 3/1992 |
| 2007/0255279 A1 | 11/2007 | Buysse et al. | | JP | 5-5106 | 1/1993 |
| 2007/0260235 A1 | 11/2007 | Podhajsky | | JP | 5-40112 | 2/1993 |
| 2007/0260238 A1 | 11/2007 | Guerra | | JP | 06343644 A2 | 12/1994 |
| 2007/0260241 A1 | 11/2007 | Dalla Betta et al. | | JP | 07265328 A2 | 10/1995 |
| 2007/0260242 A1 | 11/2007 | Dycus et al. | | JP | 08056955 A2 | 3/1996 |
| 2007/0265616 A1 | 11/2007 | Couture et al. | | JP | 08252263 A2 | 10/1996 |
| 2008/0004616 A1 | 1/2008 | Patrick | | JP | 09010223 A2 | 1/1997 |
| 2008/0009860 A1 | 1/2008 | Odom | | JP | 11244298 A2 | 9/1999 |
| 2008/0015575 A1 | 1/2008 | Odom et al. | | JP | 2000342599 A2 | 12/2000 |
| 2008/0021450 A1 | 1/2008 | Couture | | JP | 2000350732 A2 | 12/2000 |
| 2008/0033428 A1 | 2/2008 | Artale et al. | | JP | 2001008944 A2 | 1/2001 |
| 2008/0039835 A1 | 2/2008 | Johnson et al. | | JP | 2001029356 A2 | 2/2001 |
| 2008/0045947 A1 | 2/2008 | Johnson et al. | | JP | 2001128990 A2 | 5/2001 |
| 2008/0058802 A1 | 3/2008 | Couture et al. | | SU | 401367 | 10/1973 |
| 2008/0082100 A1 | 4/2008 | Orton et al. | | WO | WO89/00757 | 1/1989 |
| | | | | WO | WO 92/04873 | 4/1992 |
| | FOREIGN PATENT DOCUMENTS | | | WO | WO 92/06642 | 4/1992 |
| DE | 2415263 | 10/1975 | | WO | WO 94/08524 A | 4/1994 |
| DE | 2627679 | 1/1977 | | WO | WO94/20025 | 9/1994 |
| DE | 8712328 | 3/1988 | | WO | WO 95/02369 | 1/1995 |
| DE | 4303882 | 8/1994 | | WO | WO 95/07662 | 3/1995 |
| DE | 29616210 | 1/1997 | | WO | WO95/15124 | 6/1995 |
| DE | 19608716 | 4/1997 | | WO | WO96/05776 | 2/1996 |
| DE | 19751106 | 5/1998 | | WO | WO 96/22056 | 7/1996 |
| DE | 19751108 | 5/1999 | | WO | WO 96/13218 | 9/1996 |
| EP | 0364216 A1 | 4/1990 | | WO | WO 97/00646 | 1/1997 |
| EP | 518230 A1 | 12/1992 | | WO | WO 97/00647 | 1/1997 |
| EP | 0 541 930 B1 | 5/1993 | | WO | WO97/10764 | 3/1997 |
| EP | 0572131 | 12/1993 | | WO | WO 97/24073 | 7/1997 |
| EP | 584787 A1 | 3/1994 | | WO | WO 97/24993 | 7/1997 |
| EP | 0589453 A2 | 3/1994 | | WO | WO 98/27880 | 7/1998 |
| EP | 0623316 A1 | 11/1994 | | WO | WO 99/03407 | 1/1999 |
| EP | 0624348 A2 | 11/1994 | | WO | WO 99/03408 | 1/1999 |
| EP | 0650701 A1 | 5/1995 | | WO | WO 99/03409 | 1/1999 |
| EP | 0694290 A3 | 3/1996 | | WO | WO 99/12488 | 3/1999 |
| EP | 0717966 A1 | 6/1996 | | WO | WO 99/40857 | 8/1999 |
| EP | 0754437 A3 | 3/1997 | | WO | WO 99/40861 | 8/1999 |
| EP | 853922 A1 | 7/1998 | | WO | WO 99/51158 | 10/1999 |
| EP | 0875209 A1 | 11/1998 | | WO | WO 99/66850 | 12/1999 |
| EP | 0878169 A1 | 11/1998 | | WO | WO 99/66850 A | 12/1999 |
| EP | 0887046 A3 | 1/1999 | | WO | WO 00/24330 | 5/2000 |
| EP | 0923907 A1 | 6/1999 | | WO | WO00/24331 | 5/2000 |
| EP | 0986990 A1 | 3/2000 | | WO | WO 00/41638 | 7/2000 |
| EP | 1034747 A1 | 9/2000 | | WO | WO00/47124 | 8/2000 |
| EP | 1034748 A1 | 9/2000 | | WO | WO 00/53112 | 9/2000 |
| EP | 1025807 A3 | 10/2000 | | WO | WO 01/17448 A | 3/2001 |
| EP | 1034746 A3 | 10/2000 | | WO | WO 01/54604 | 8/2001 |
| EP | 1050278 A1 | 11/2000 | | WO | WO02/07627 | 1/2002 |
| EP | 1053719 A1 | 11/2000 | | WO | WO 02/07627 | 1/2002 |
| EP | 1053720 A1 | 11/2000 | | WO | WO 02/067798 A1 | 9/2002 |
| EP | 1055399 A1 | 11/2000 | | WO | WO02/080783 | 10/2002 |
| EP | 1055400 A1 | 11/2000 | | WO | WO 02/080783 | 10/2002 |
| EP | 1080694 A1 | 3/2001 | | WO | WO 02/080784 | 10/2002 |
| EP | 1082944 A1 | 3/2001 | | WO | WO02/080784 | 10/2002 |
| EP | 1159926 A2 | 12/2001 | | WO | WO 02/080785 | 10/2002 |
| EP | 1301135 A | 4/2003 | | WO | WO02/080785 | 10/2002 |
| EP | 1330991 A1 | 7/2003 | | WO | WO02/080786 | 10/2002 |
| EP | 1486177 A2 | 6/2004 | | WO | WO 02/080793 | 10/2002 |
| EP | 1472984 A1 | 11/2004 | | WO | WO02/080793 | 10/2002 |
| EP | 1527747 A2 | 5/2005 | | WO | WO02/080794 | 10/2002 |
| EP | 1530952 A1 | 5/2005 | | WO | WO 02/080794 | 10/2002 |
| EP | 1532932 A1 | 5/2005 | | WO | WO 02/080795 | 10/2002 |
| EP | 1535581 A2 | 6/2005 | | WO | WO 02/080796 | 10/2002 |
| EP | 1609430 A1 | 12/2005 | | WO | WO 02/080796 A1 | 10/2002 |
| EP | 1632192 A1 | 3/2006 | | WO | WO 02/080797 | 10/2002 |
| EP | 1645238 A1 | 4/2006 | | WO | WO02/080797 | 10/2002 |
| EP | 1645240 A2 | 4/2006 | | WO | WO 02/080798 A1 | 10/2002 |
| EP | 1707143 A1 | 10/2006 | | WO | WO 02/080799 | 10/2002 |
| GB | 2214430 A | 6/1989 | | WO | WO02/081170 | 10/2002 |
| | | | | WO | WO 02/081170 | 10/2002 |

| | | |
|---|---|---|
| WO | WO/080786 | 10/2002 |
| WO | WO 03/090630 A3 | 11/2003 |
| WO | WO 03/101311 | 12/2003 |
| WO | WO 2004/032776 A1 | 4/2004 |
| WO | WO 2004/032777 | 4/2004 |
| WO | WO2004/032777 | 4/2004 |
| WO | WO 2004/052221 A1 | 6/2004 |
| WO | WO 2004/073488 A2 | 9/2004 |
| WO | WO2004/073490 | 9/2004 |
| WO | WO 2004/073490 | 9/2004 |
| WO | WO2004/073753 | 9/2004 |
| WO | WO 2004/082495 | 9/2004 |
| WO | WO 2004/082495 A1 | 9/2004 |
| WO | WO 2004/098383 A1 | 11/2004 |
| WO | WO 2004/103156 | 12/2004 |
| WO | WO 2005/004734 A1 | 1/2005 |
| WO | WO2005/004735 | 1/2005 |
| WO | WO 2005/110264 | 11/2005 |

OTHER PUBLICATIONS

Bergdahl et al. "Studies on Coagulation and the Development of an Automatic Computerized Bipolar Coagulator" J.Neurosurg, vol. 75, Jul. 1991, pp. 148-151.

Kennedy et al. "High-burst-strength, feedback-controlled bipolar vessel sealing" Surgical Endoscopy (1998) 12: 876-878.

Peterson et al. "Comparison of Healing Process Following Ligation with Sutures and Bipolar Vessel Sealing" Surgical Technology International (2001).

Linehan et al. "A Phase I Study of the LigaSure Vessel Sealing System in Hepatic Surgery" Section of HPB Surger, Washington University School of Medicine, St. Louis MO, Presented at AHPBA, Feb. 2001.

Johnson et al. "Evaluation of the LigaSure Vessel Sealing System in Hemorrhoidectomy" American College of Surgeons (ACS) Clinicla Congress Poster (2000).

Sayfan et al. "Sutureless Closed Hemorrhoidectomy: A New Technique" Annals of Surgery vol. 234 No. 1 Jul. 2001 pp. 21-24.

Heniford et al. "Initial Results with an Electrothermal Bipolar Vessel Sealer" Surgical Endoscopy (2000) 15:799-801.

Heniford et al. "Initial Research and Clinical Results with an Electrothermal Bipolar Vessel Sealer" Oct. 1999.

McLellan et al. "Vessel Sealing for Hemostasis During Pelvic Surgery" Int'l Federation of Gynecology and Obstetrics Figo World Congress 2000, Washington, D.C.

Levy et al. "Use of a New Energy-based Vessel Ligation Device During Vaginal Hysterectomy" Int'l Federation of Gynecology and Obstetrics (FIGO) World Congress 1999.

Crawford et al. "Use of the LigaSure Vessel Sealing System in Urologic Cancer Surger" Grand Rounds in Urology 1999 vol. 1 Issue 4 pp. 10-17.

Rothenberg et al. "Use of the LigaSure Vessel Sealing System in Minimally Invasive Surgery in Children" Int'l Pediatric Endosurgery Group (IPEG) 2000.

Palazzo et al. "Randomized clinical trial of Ligasure versus open haemorrhoidectomy" British Journal of Surgery 2002, 89, 154-157.

"Innovations in Electrosurgery" Sales/Product Literature; Dec. 31, 2000.

LigaSure Vessel Sealing System, the Seal of Confidence in General, Gynecologic, Urologic, and Laparaoscopic Surgery Sales/Product Literature; Jan. 2004.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC 2003.

"Reducing Needlestick Injuries in the Operating Room" Sales/Product Literature 2001.

Chung et al., "Clinical Experience of Sutureless Closed Hemorrhoidectomy with LigaSure" Diseases of the Colon & Rectum vol. 46, No. 1 Jan. 2003.

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

Paul G. Horgan, "A Novel Technique for Parencymal Division During Hepatectomy" The American Journal of Surgery, vol. 181, No. 3, Apr. 2001 pp. 236-237.

W. Scott Helton, "LigaSure Vessel Sealing System: Revolutionary Hemostasis Product for General Surgery" Sales/Product Literature 1999.

Michael Choti, "Abdominoperineal Resection with the LigaSure Vessel Sealing System and LigaSure Atlas 20 cm Open Instrument" Innovations That Work, Jun. 2003.

Craig Johnson, "Use of the LigaSure Vessel Sealing System in Bloodless Hemorrhoidectomy" Innovations That Work, Mar. 2000.

Muller et al., "Extended Left Hemicolectomy Using the LigaSure Vessel Sealing System" Innovations That Work, Sep. 1999.

Herman et al., "Laparoscopic Intestinal Resection With the LigaSure Vessel Sealing System: A Case Report" Innovations That Work, Feb. 2002.

Carus et al., "Initial Experience With The LigaSure Vessel Sealing System in Abdominal Surgery" Innovations That Work, Jun. 2002.

Levy et al. "Randomized Trial of Suture Versus Electrosurgical Bipolar Vessel Sealing in Vaginal Hysterectomy" Obstetrics & Gynecology, vol. 102, No. 1, Jul. 2003.

Levy et al., "Update on Hysterectomy—New Technologies and Techniques" OBG Management, Feb. 2003.

Barbara Levy, "Use of a New Vessel Ligation Device During Vaginal Hysterectomy" FIGO 2000, Washington, D.C.

McLellan et al. "Vessel Sealing For Hemostasis During Gynecologic Surgery" Sales/Product Literature 1999.

Sengupta et al., "Use of a Computer-Controlled Bipolar Diathermy System in Radical Prostatectomies and Other Open Urological Surgery" ANZ Journal of Surgery (2001) 71.9 pp. 538-540.

Olsson et al. "Radical Cystectomy in Females" Current Surgical Techniques in Urology, vol. 14, Issue 3, 2001.

E. David Crawford "Use of a Novel Vessel Sealing Technology in Management of the Dorsal Veinous Complex" Sales/Product Literature 2000.

Jarrett et al., "Use of the LigaSure Vessel Sealing System for Peri-Hilar Vessels in Laparoscopic Nephrectomy" Sales/Product Literature 2000.

E. David Crawford "Evaluation of a New Vessel Sealing Device in Urologic Cancer Surgery" Sales/Product Literature 2000.

Joseph Ortenberg "LigaSure Used in Laparoscopic 1st and 2nd Stage Orchiopexy" Innovations That Work, Nov. 2002.

Koyle et al., "Laparoscopic Palomo Varicocele Ligation in Children and Adolescents" Pediatric Endosurgery & Innovative Techniques, vol. 6, No. 1, 2002.

Dulemba et al. "Use of a Bipolar Electrothermal Vessel Sealer in Laparoscopically Assisted Vaginal Hysterectomy" Sales/Product Literature; Jan. 2004.

Johnson et al. "Evaluation of a Bipolar electrothermal Vessel Sealing Device in Hemorrhoidectomy" Sales/Product Literature; Jan. 2004.

Int'l Search Report PCT/US98/18640.
Int'l Search Report PCT/US98/23950.
Int'l Search Report PCT/US99/24869.
Int'l Search Report PCT/US01/11218.
Int'l Search Report PCT/US01/11340.
Int'l Search Report PCT/US01/11420.
Int'l Search Report PCT/US02/01890.
Int'l Search Report PCT/US02/11100.
Int'l Search Report PCT/US04/03436.
Int'l Search Report PCT/US04/13273.
Int'l Search Report PCT/US04/15311.
Int'l Search Report EP 98944778.
Int'l Search Report EP 98958575.
Int'l Search Report EP 04027314.
Int'l Search Report EP 04027479.
Int'l Search Report EP 04027705.
Int'l Search Report EP 04013772.
Int'l Search Report EP 05016399 dated Jan. 5, 2006.
Int'l Search Report EP 06005185.1 dated Apr. 18, 2006.
Int'l Search Report EP 06008779.8 dated Jun. 13, 2006.
Int'l Search Report EP 1683496 dated Jun. 13, 2006.
Int'l Search Report EP 04013772 dated Apr. 1, 2005.
Int'l Search Report EP 05013895 dated Oct. 14, 2005.

Int'l Search Report EP 05017281 dated Nov. 16, 2005.
Int'l Search Report EP 06006716 dated Aug. 4, 2006.
Int'l Search Report PCT/US01/11224 dated Nov. 13, 2001.
Int'l Search Report EP 06014461.5 dated Oct. 20, 2006.
Int'l Search Report EP 06020584.6 dated Jan. 12, 2007.
Int'l Search Report EP 06020583.8 dated Jan. 30, 2007.
Int'l Search Report EP 06020756.0 dated Feb. 5, 2007.
Int'l Search Report EP 06024123.9 dated Feb. 26, 2007.
Int'l Search Report EP 05013463.4 dated Sep. 28, 2005.
Int'l Search Report EP 05019130.3 dated Oct. 18, 2005.
Int'l Search Report EP 05020665.5 dated Feb. 16, 2006.
Int'l Search Report EP 05020666.3 dated Feb. 17, 2006.
Int'l Search Report EP 05021779.3 dated Jan. 18, 2006.
Int'l Search Report EP 05021197.8 dated Jan. 31, 2006.
Int'l Search Report EP 0502137.7 dated Jan. 13, 2006.
Int'l Search Report—extended- EP 05021937.7 dated Mar. 6, 2006.
Int'l Search Report EP 05023017.6 dated Feb. 16, 2006.
Int'l Search Report EP 05021780.1 dated Feb. 9, 2006.
Int'l Search Report EP 06002279.5 dated Mar. 22, 2006.
Int'l Search Report EP 04 752343.6 dated Jul. 20, 2007.
Int'l Search Report EP 06 024122.1 dated Mar. 19, 2007.
Int'l Search Report EP 07 001480.8 dated Apr. 12, 2007.
Int'l Search Report EP 07 001488.1 dated May 29, 2007.
Int'l Search Report—Extended EP 07 009029.5 dated Jul. 12, 2007.
Int'l Search Report EP 07 009321.6 dated Aug. 17, 2007.
Int'l Search Report EP 06 020574.7 dated Sep. 21, 2007.
Int'l Search Report EP 07 010672.9 dated Oct. 1, 2007.
Int'l Search Report EP 07 013779.9 dated Oct. 18, 2007.
Int'l Search Report EP 07 009026.1 dated Sep. 12, 2007.
Int'l Search Report EP 07 015601.3 dated Dec. 6, 2007.
Int'l Search Report EP 07 015191.5 dated Dec. 19, 2007.
Int'l Search Report EP 07 020283.3 dated Jan. 16, 2008.

* cited by examiner

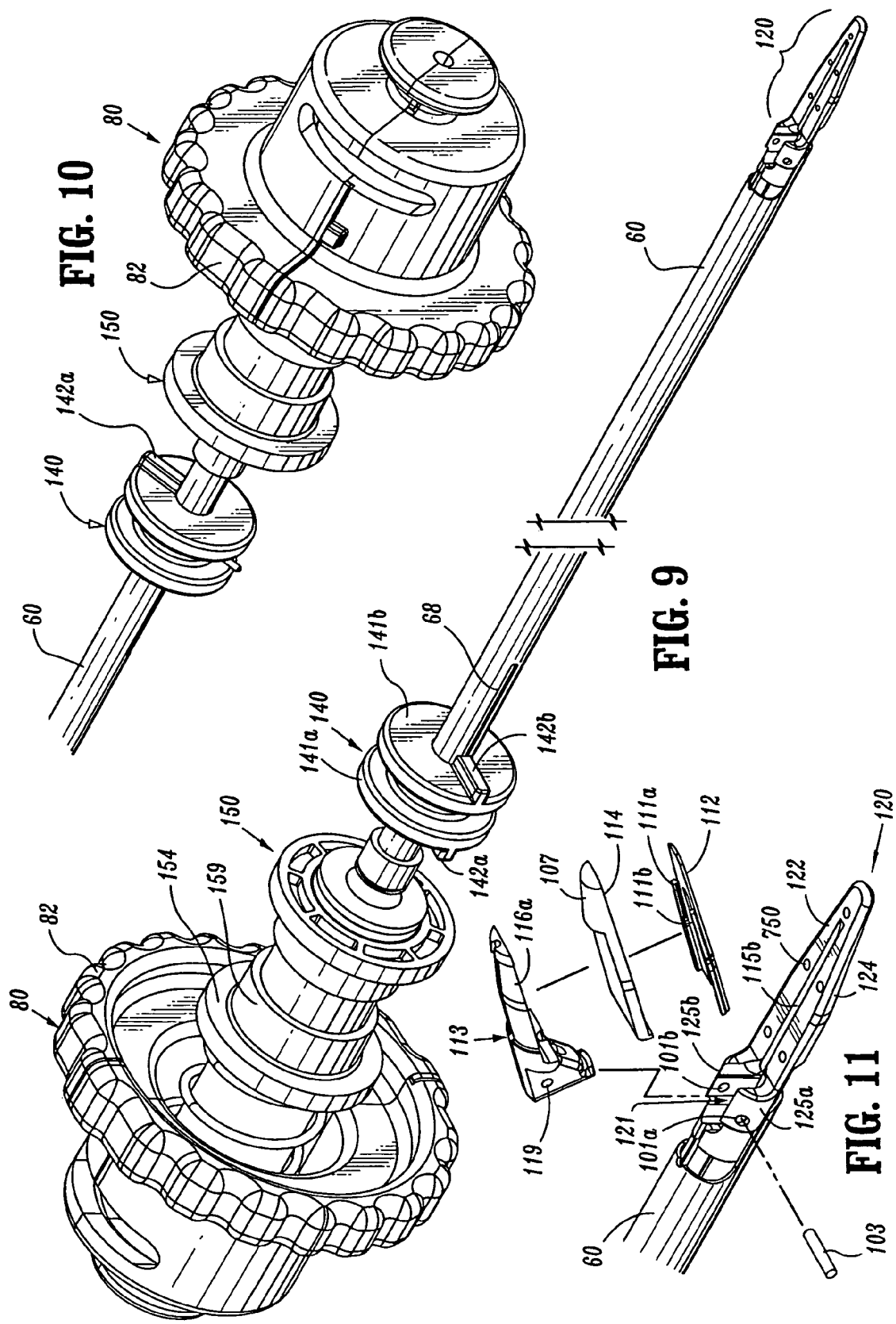

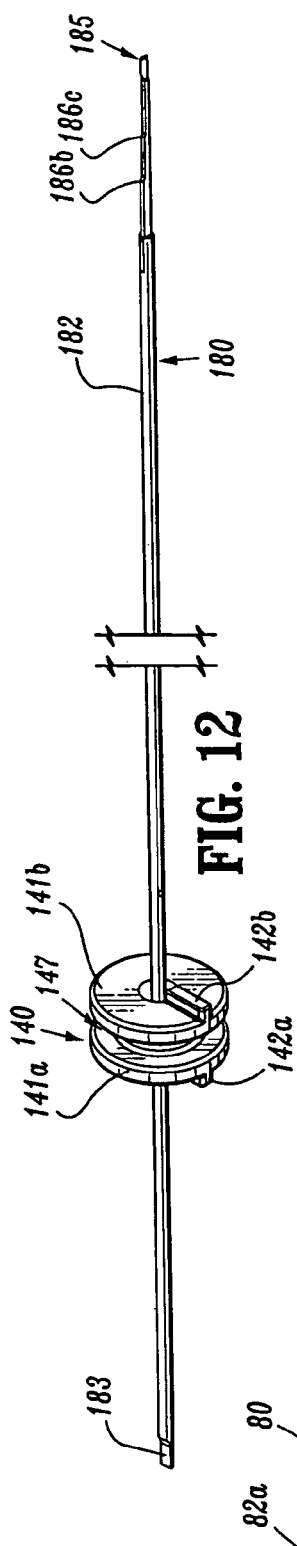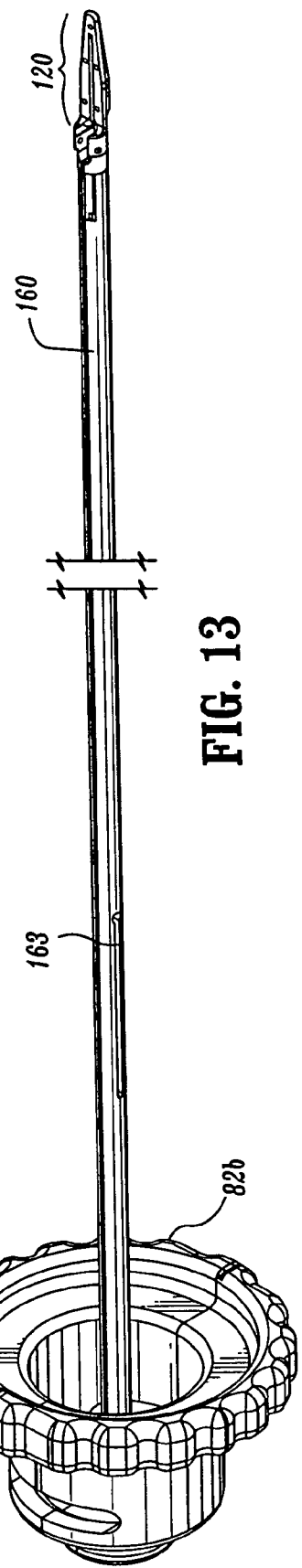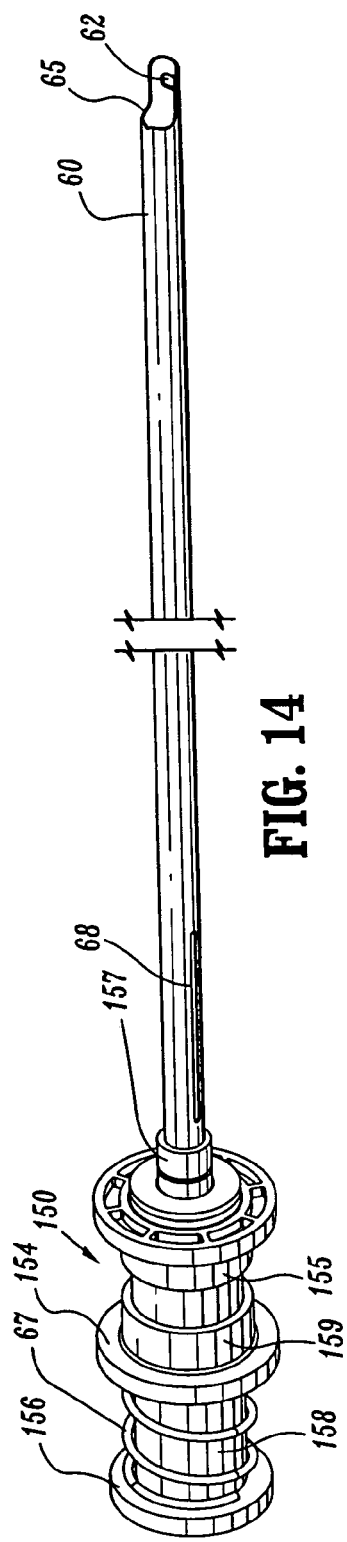

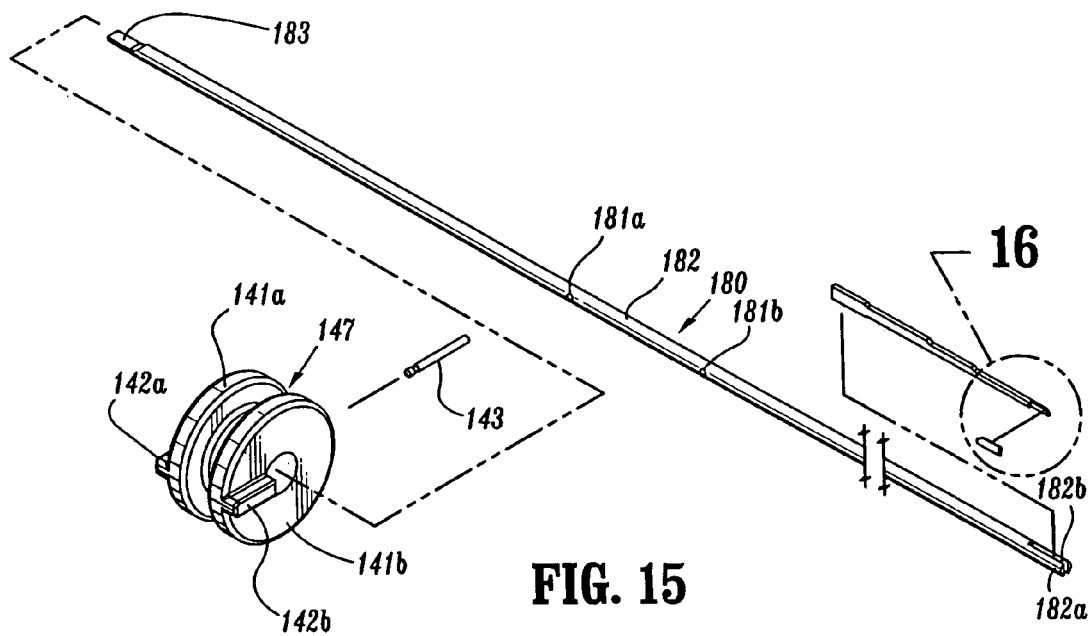
FIG. 15
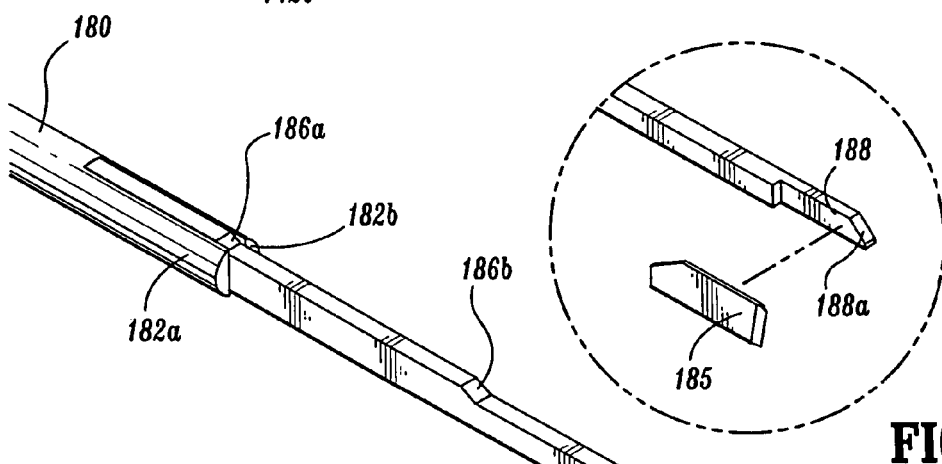
FIG. 16
FIG. 17
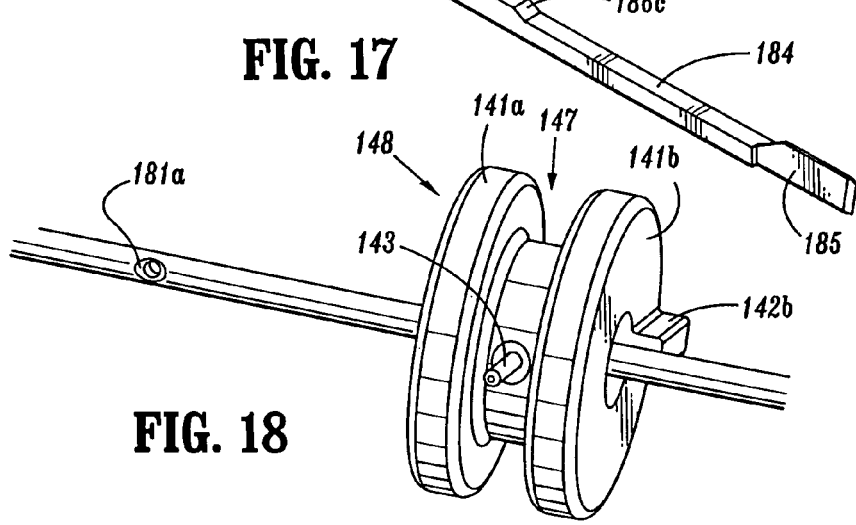
FIG. 18

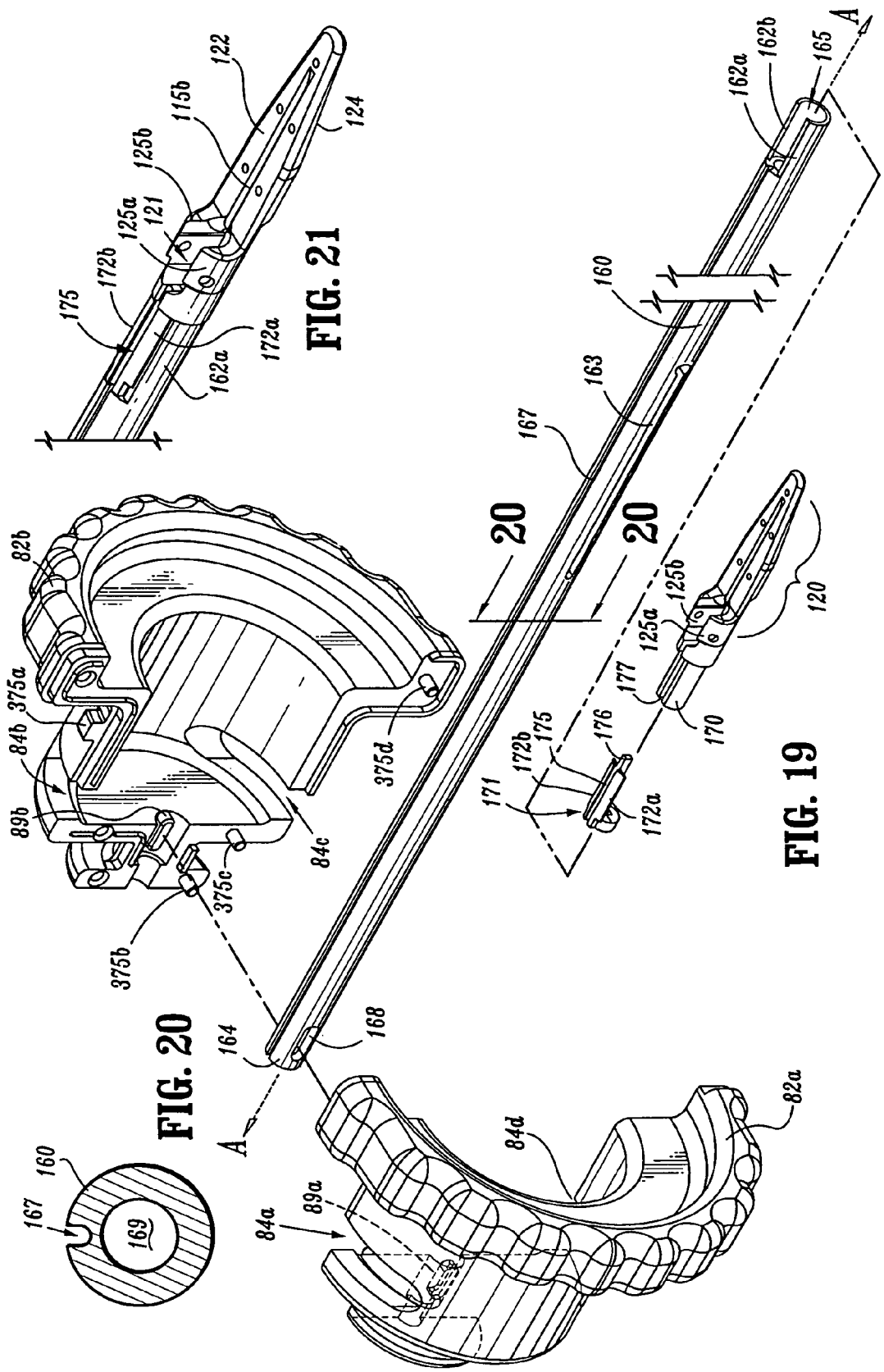

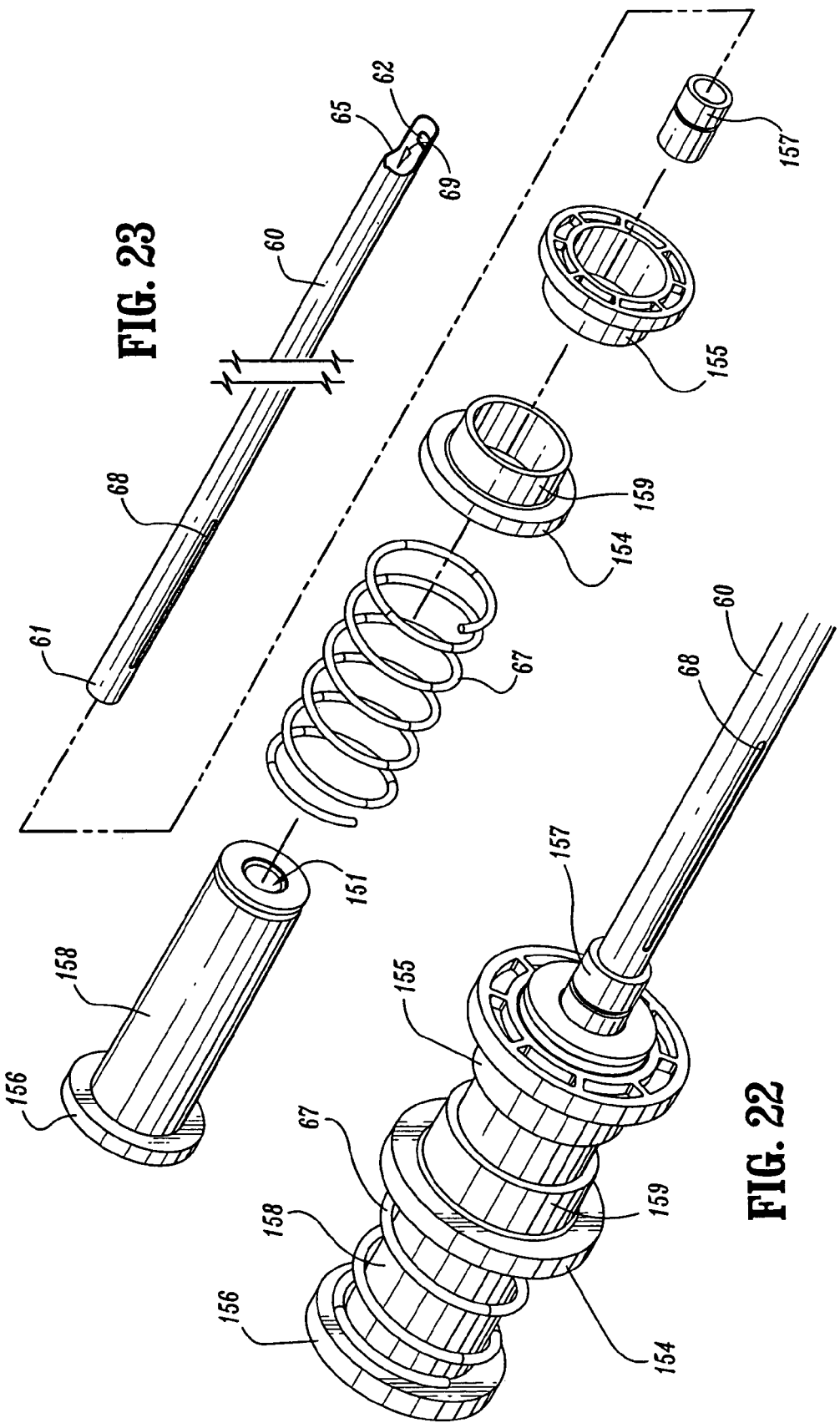

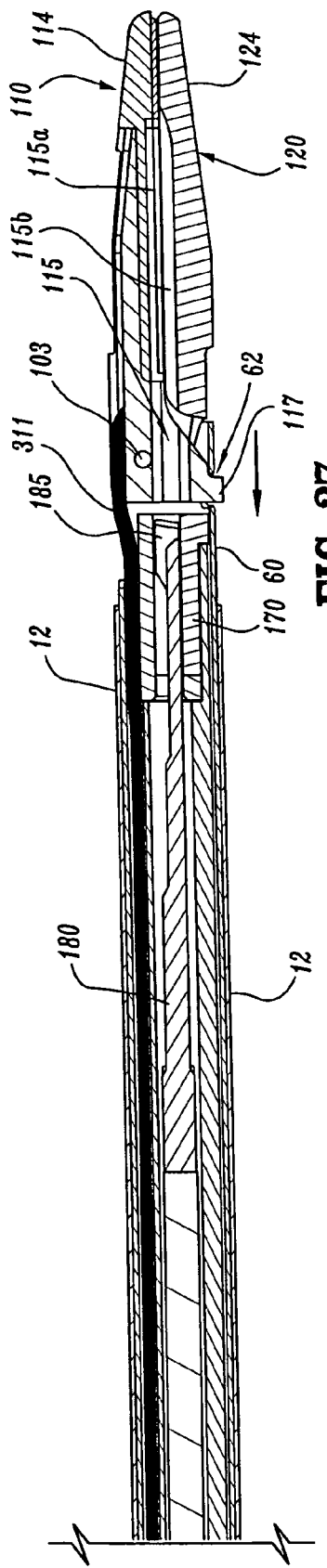
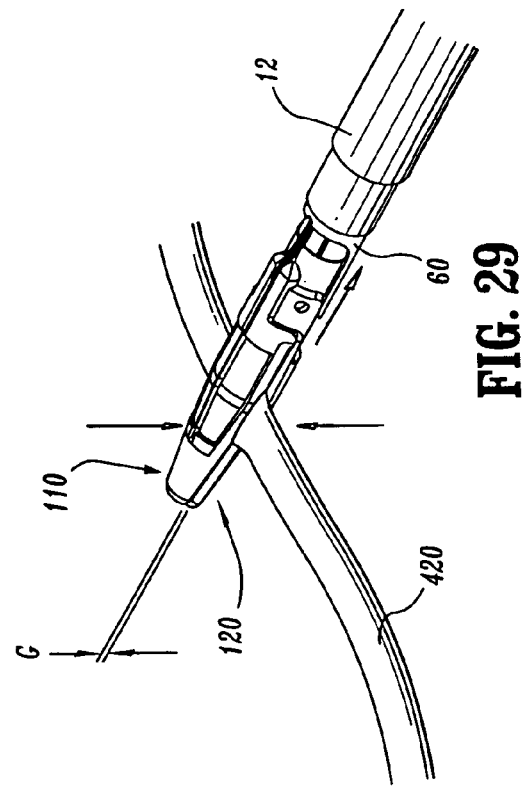
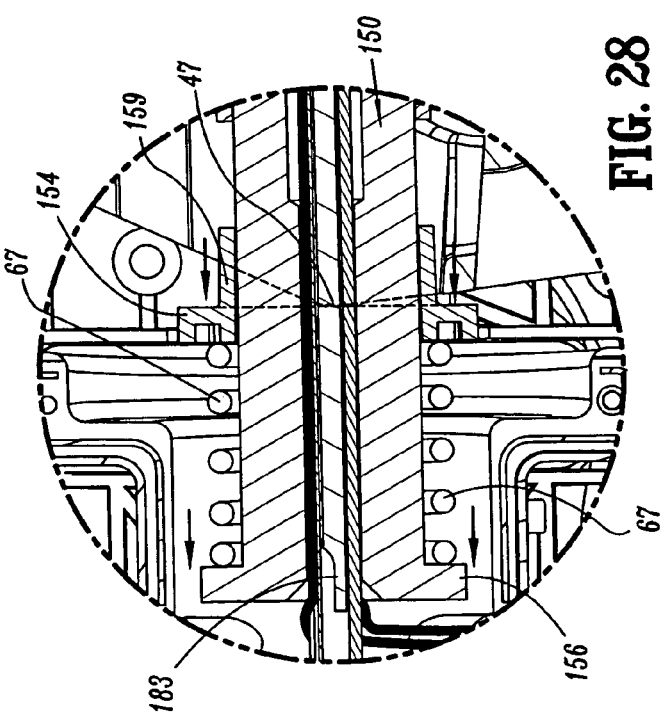

SINGLE ACTION TISSUE SEALER

BACKGROUND

The present disclosure relates to an electrosurgical forceps and more particularly, the present disclosure relates to an endoscopic bipolar electrosurgical forceps for manipulating, clamping, sealing and cutting tissue in a single action.

TECHNICAL FIELD

Electrosurgical forceps utilize both mechanical clamping action and electrical energy to affect hemostasis by heating the tissue and blood vessels to coagulate, cauterize and/or seal tissue. As an alternative to open forceps for use with open surgical procedures, many modern surgeons use endoscopes and endoscopic instruments for remotely accessing organs through smaller, puncture-like incisions. As a direct result thereof, patients tend to benefit from less scarring and reduced healing time.

Endoscopic instruments are inserted into the patient through a cannula, or port, which has been made with a trocar. Typical sizes for cannulas range from about three millimeters to about 12 millimeters. Smaller cannulas are usually preferred, which, as can be appreciated, ultimately presents a design challenge to instrument manufacturers who look for ways to make endoscopic instruments that fit through the smaller cannulas.

Many endoscopic surgical procedures require cutting or ligating blood vessels or vascular tissue. Due to the inherent spatial considerations of the surgical cavity, surgeons often have difficulty suturing vessels or performing other traditional methods of controlling bleeding, e.g., clamping and/or tying-off transected blood vessels. By utilizing an endoscopic electrosurgical forceps, a surgeon can either cauterize, coagulate/desiccate and/or simply reduce or slow bleeding simply by controlling the intensity, frequency and duration of the electrosurgical energy applied through the jaw members to the tissue. Most small blood vessels, i.e., in the range below two millimeters in diameter, can often be closed using standard electrosurgical instruments and techniques. However, if a larger vessel is ligated, it may be necessary for the surgeon to convert the endoscopic procedure into an open-surgical procedure and thereby abandon the benefits of endoscopic surgery. Alternatively, the surgeon can seal the larger vessel or tissue.

It is thought that the process of coagulating vessels is fundamentally different from electrosurgical vessel sealing. For the purposes herein, "coagulation" is defined as a process of desiccating tissue wherein the tissue cells are ruptured and dried. "Vessel sealing" or "tissue sealing" is defined as the process of liquefying the collagen in the tissue so that it reforms into a fused mass. Coagulation of small vessels is sufficient to permanently close them, while larger vessels need to be sealed to assure permanent closure.

In order to effectively seal larger vessels (or tissue) two predominant mechanical parameters should be accurately controlled—the pressure applied to the vessel (tissue) and the gap distance between the electrodes—both of which are affected by the thickness of the sealed vessel. More particularly, accurate application of pressure is important to oppose the walls of the vessel; to reduce the tissue impedance to a low enough value that allows enough electrosurgical energy through the tissue; to overcome the forces of expansion during tissue heating; and to contribute to the end tissue thickness which is an indication of a good seal. It has been determined that a typical fused vessel wall is optimum between about 0.001 and about 0.006 inches. Below this range, the seal may shred or tear and above this range the lumens may not be properly or effectively sealed.

With respect to smaller vessels, the pressure applied to the tissue tends to become less relevant whereas the gap distance between the electrically conductive surfaces becomes more significant for effective sealing. In other words, the chances of the two electrically conductive surfaces touching during activation increases as vessels become smaller.

As mentioned above, in order to properly and effectively seal larger vessels or tissue, a greater closure force between opposing jaw members is required. It is known that a large closure force between the jaws typically requires a large moment about the pivot for each jaw. This presents a design challenge because the jaw members are typically affixed with pins which are positioned to have small moment arms with respect to the pivot of each jaw member. A large force, coupled with a small moment arm, is undesirable because the large forces may shear the pins. As a result, designers compensate for these large closure forces by either designing instruments with metal pins and/or by designing instruments which at least partially offload these closure forces to reduce the chances of mechanical failure. As can be appreciated, if metal pivot pins are employed, the metal pins should be insulated to avoid the pin acting as an alternate current path between the jaw members which may prove detrimental to effective sealing.

Increasing the closure forces between electrodes may have other undesirable effects, e.g., it may cause the opposing electrodes to come into close contact with one another which may result in a short circuit and a small closure force may cause pre-mature movement of the tissue during compression and prior to activation. As a result thereof, providing an instrument which consistently provides the appropriate closure force between opposing electrodes within a preferred pressure range will enhance the chances of a successful seal. As can be appreciated, relying on a surgeon to manually provide the appropriate closure force within the appropriate range on a consistent basis would be difficult and the resultant effectiveness and quality of the seal may vary. Moreover, the overall success of creating an effective tissue seal is greatly reliant upon the user's expertise, vision, dexterity, and experience in judging the appropriate closure force to uniformly, consistently and effectively seal the vessel. In other words, the success of the seal would greatly depend upon the ultimate skill of the surgeon rather than the efficiency of the instrument.

It has been found that the pressure range for assuring a consistent and effective seal is between about 3 kg/cm$^2$ to about 16 kg/cm$^2$ and, desirably, within a working range of about 7 kg/cm$^2$ to about 13 kg/cm$^2$. Manufacturing an instrument which is capable of providing a closure pressure within this working range has been shown to be effective for sealing arteries, tissues and other vascular bundles.

Various force-actuating assemblies have been developed in the past for providing the appropriate closure forces to affect vessel sealing. For example, one such actuating assembly has been developed by Valleylab, Inc., of Boulder Colo., a division of Tyco Healthcare LP, for use with Valleylab's vessel sealing and dividing instrument commonly sold under the trademark LIGASURE ATLAS®. This assembly includes a four-bar mechanical linkage, a spring and a drive assembly which cooperate to consistently provide and maintain tissue pressures within the above working ranges. The LIGASURE ATLAS® is presently designed to fit through a 10 mm cannula and includes a bi-lateral jaw closure mechanism which is activated by a foot switch. A trigger assembly extends a knife distally to separate the tissue along the tissue seal. A rotating mechanism is associated with distal end of the handle to allow a surgeon to selectively rotate the jaw members to facilitate grasping tissue. Co-pending U.S. application Ser. Nos. 10/179,863 and 10/116,944 and PCT Application Serial Nos. PCT/US01/01890 and PCT/7201/11340 describe in detail the operating features of the LIGASURE ATLAS® and various methods relating thereto. The contents of all of these applications are hereby incorporated by reference herein.

It would be desirous to develop an instrument that reduces the number of steps it takes to perform the tissue seal and cut. Preferably, the instrument would be able to manipulate, clamp, seal and cut tissue in a single action (e.g., by squeezing a handle).

SUMMARY

The present disclosure relates to an endoscopic bipolar forceps which includes a housing and a shaft affixed to the distal end of the housing. Preferably, the shaft includes a diameter such that the shaft is freely insertable through a trocar. The shaft also includes a longitudinal axis defined therethrough and a pair of first and second jaw members attached to a distal end thereof. The forceps includes a drive assembly for moving the first jaw member relative to the second member from a first position wherein the jaw members are disposed in spaced relation relative to each other to a second position wherein the jaw members cooperate to grasp tissue therebetween. A movable handle is included which is rotatable about a pivot located above the longitudinal axis of the shaft. Movement of the movable handle mechanically cooperates with internal components to move the jaw members from the open and closed positions, to clamp tissue, to seal tissue and to cut tissue. Advantageously, the pivot is located a fixed distance above the longitudinal axis to provide lever-like mechanical advantage to a drive flange of the drive assembly. The drive flange is located generally along the longitudinal axis. The forceps is connected to a source of electrosurgical energy which carries electrical potentials to each respective jaw member such that the jaw members are capable of conducting bipolar energy through tissue held therebetween to affect a tissue seal.

The forceps includes a switch disposed within the housing which is electromechanically connected to the energy source. Advantageously, the switch allows a user to supply bipolar energy to the jaw members to affect a tissue seal. The switch is activated by contact from a cutter lever or the movable handle itself when a user continues to compress the movable handle after the tissue has been clamped.

The forceps includes an advanceable knife assembly for cutting tissue in a forward direction along the tissue seal. The knife assembly is advanced when a user continues to compress the movable handle after the tissue has been sealed, forcing the cutter lever forward. A rotating assembly may also be included for rotating the jaw members about the longitudinal axis defined through the shaft.

In one embodiment, the movable jaw member includes a first electrical potential and the fixed jaw member includes a second electrical potential. A lead connects the movable jaw member to the first potential and a conductive tube (which is disposed through the shaft) conducts a second electrical potential to the fixed jaw member. Advantageously, the conductive tube is connected to the rotating assembly to permit selective rotation of the jaw members.

In one embodiment, the drive assembly includes a reciprocating sleeve which upon activation of the movable handle, translates atop the rotating conductive tube to move the movable jaw member relative to the fixed jaw member. In one embodiment, the movable jaw member includes a detent which extends beyond the fixed jaw member which is designed for engagement with the reciprocating sleeve such that, upon translation thereof, the movable jaw member moves relative to the fixed jaw member. Advantageously, a spring is included with the drive assembly to facilitate actuation of the movable handle and to ensure the closure force is maintained within the working range of about 3 kg/cm$^2$ to about 16 kg/cm$^2$ and, preferably, about 7 kg/cm$^2$ to about 13 kg/cm$^2$.

In one embodiment, at least one of the jaw members includes a series of stop members disposed thereon for regulating the distance between the jaw members (i.e., creating a gap between the two opposing jaw members) during the sealing process. As can be appreciated, regulating the gap distance between opposing jaw members along with maintaining the closing pressure to within the above-described ranges will produce a reliable and consistent tissue seal.

The present disclosure also relates to an endoscopic bipolar forceps which includes a shaft having a movable jaw member and a fixed jaw member at a distal end thereof. The forceps also includes a drive assembly for moving the movable jaw member relative to the fixed jaw member from a first position wherein the movable jaw member is disposed in spaced relation relative to the fixed jaw member to a second position wherein the movable jaw member is closer to the fixed jaw member for manipulating tissue. A movable handle is included which actuates the drive assembly to move the movable jaw member.

The forceps connects to a source of electrosurgical energy which is conducted to each jaw member such that the jaw members are capable of conducting bipolar energy through tissue held therebetween to affect a tissue seal. Advantageously, the forceps also includes a selectively advanceable knife assembly for cutting tissue in a distal direction along the tissue seal and a stop member disposed on at least one of the jaw members for regulating the distance between jaw members during sealing.

BRIEF DESCRIPTION OF THE DRAWINGS

Various embodiments of the subject instrument are described herein with reference to the drawings wherein:

FIG. 9 is a left, perspective view of a rotating assembly, drive assembly, knife assembly and lower jaw member according to the present disclosure;

FIG. 10 is a rear, perspective view of the rotating assembly, drive assembly and knife assembly;

FIG. 11 is an enlarged, top, perspective view of the end effector assembly with parts separated;

FIG. 12 is an enlarged, perspective view of the knife assembly;

FIG. 13 is an enlarged, perspective view of the rotating assembly;

FIG. 14 is an enlarged, perspective view of the drive assembly;

FIG. 15 is an enlarged, perspective view of the knife assembly with parts separated;

FIG. 16 is an enlarged view of the indicated area of detail of FIG. 15;

FIG. 17 is a greatly-enlarged, perspective view of a distal end of the knife assembly;

FIG. 18 is a greatly-enlarged, perspective view of a knife drive of the knife assembly;

FIG. 19 is an enlarged, perspective view of the rotating assembly and low jaw member with parts separated;

FIG. 20 is a cross section along line 20-20 of FIG. 19;

FIG. 21 is a greatly-enlarged, perspective view of the lower jaw member;

FIG. 22 is an enlarged, perspective view of the drive assembly;

FIG. 23 is an enlarged perspective view of the drive assembly of FIG. 22 with parts separated;

FIG. 27 is a greatly-enlarged view of an end effector;

FIG. 28 is a greatly-enlarged view of the drive assembly;

FIG. 29 is an enlarged, rear, perspective view of the end effector shown grasping tissue;

DETAILED DESCRIPTION

Figure 1:
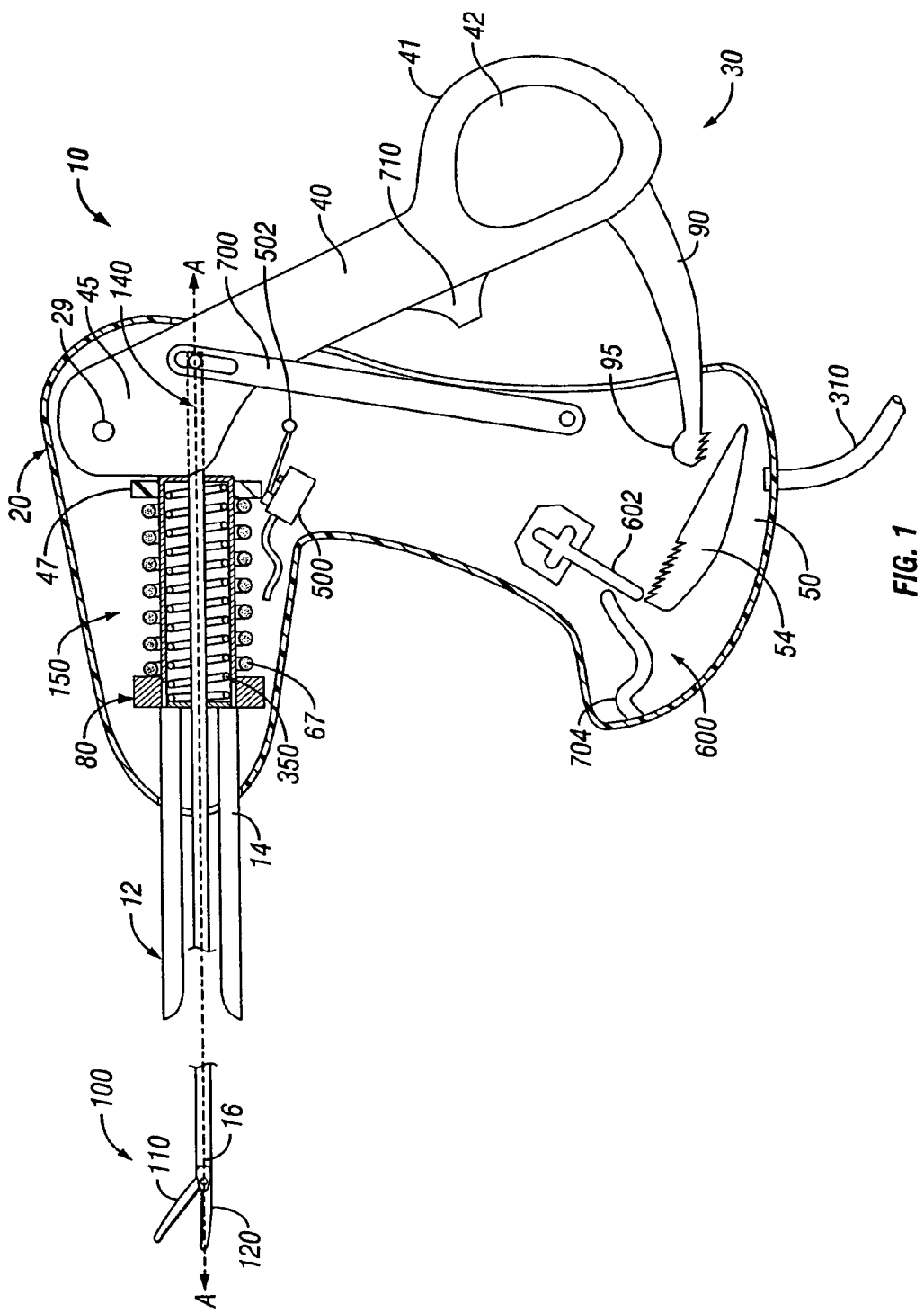
FIG. 1 is a partial schematic view of one embodiment of an endoscopic bipolar forceps having a movable thumb handle in an unactuated position according to one aspect of the present disclosure.
Figure 2:
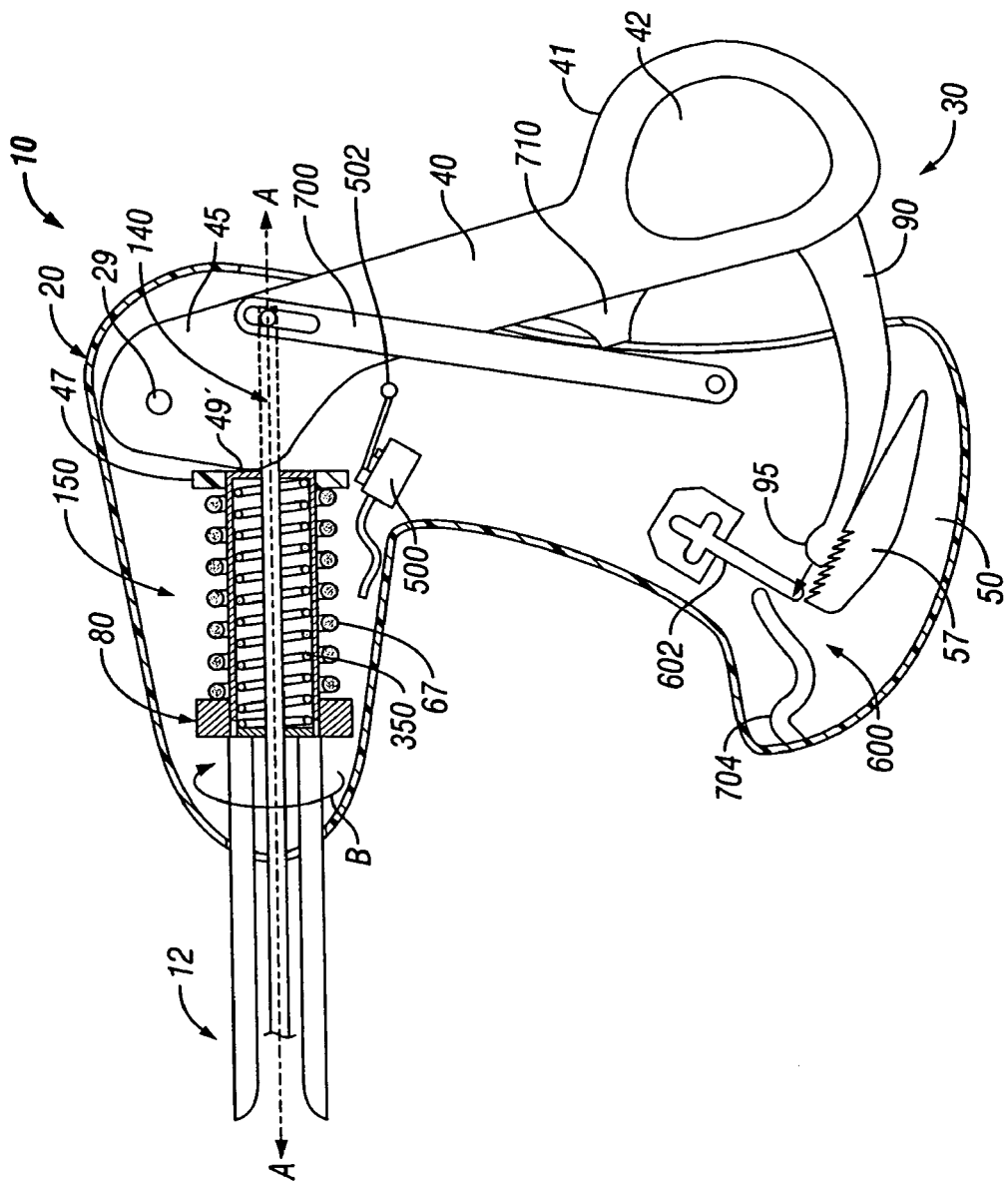
FIG. 2 is a partial schematic view of the forceps of FIG. 1 illustrated in a partially actuated position.
Figure 3:
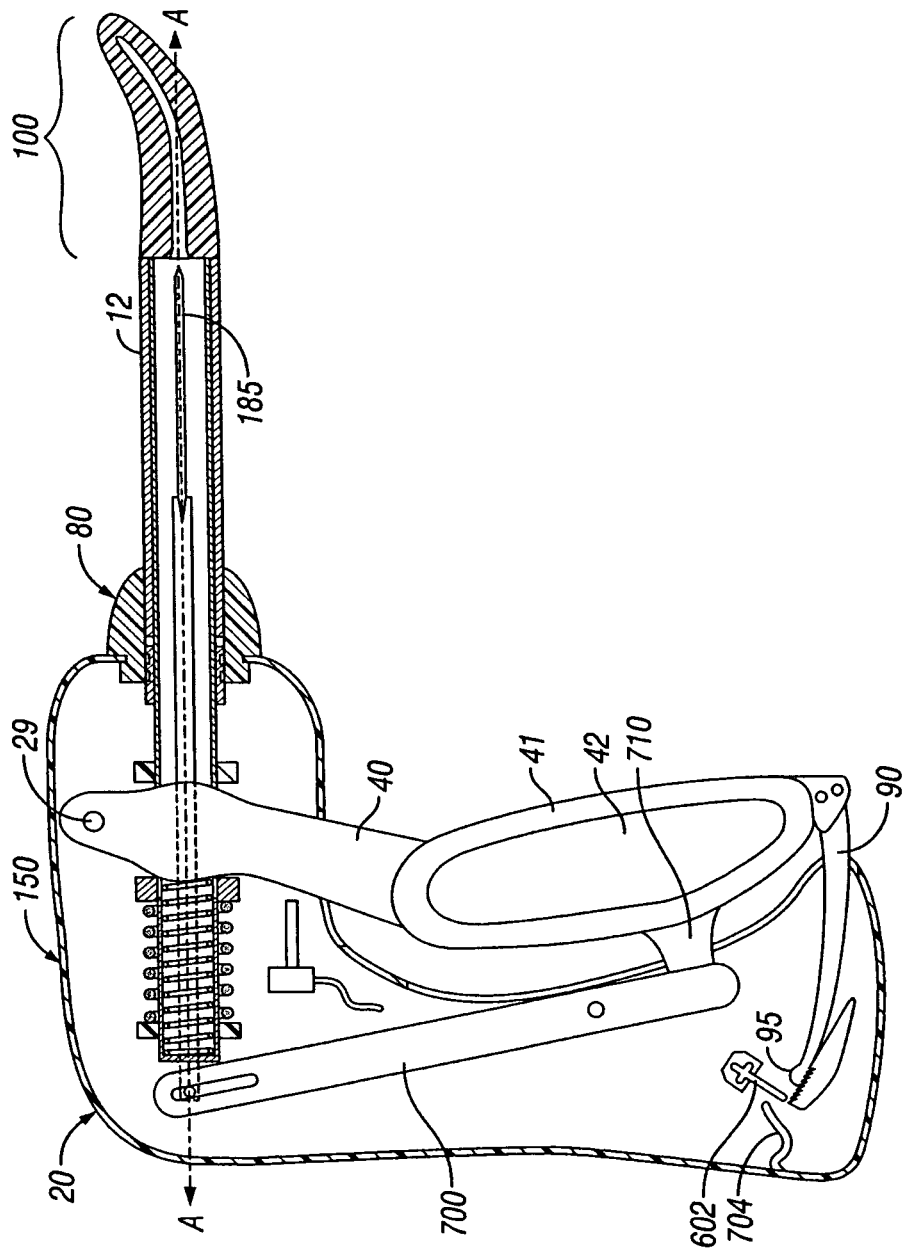
FIG. 3 is a partial schematic view of another embodiment of an endoscopic bipolar forceps having a movable finger handle illustrated in a partially actuated position.

Turning now to FIGS. 1-3, one embodiment of an endoscopic bipolar forceps 10 is shown for use with various surgical procedures and generally includes a housing 20, a handle assembly 30, a rotating assembly 80, an end effector assembly 100, a knife assembly 140 (see FIGS. 10, 12, 15-18), a drive assembly 150, a switch 500 and a latch assembly 600 which all mutually cooperate to grasp, seal and divide tubular vessels and vascular tissue 420 (FIG. 29). Although the majority of the figure drawings depict a bipolar forceps 10 for use in connection with endoscopic surgical procedures, the present disclosure may be used for more traditional open surgical procedures. For the purposes herein, the forceps 10 is described in terms of an endoscopic instrument, however, it is contemplated that an open version of the forceps may also include the same or similar operating components and features as described below.

Forceps 10 includes a shaft 12 which has a distal end 16 dimensioned to mechanically engage the end effector assembly 100 and a proximal end 14 which mechanically engages the housing 20. In the drawings and in the descriptions which follow, the term "proximal," as is traditional, will refer to the end of the forceps 10 which is closer to the user, while the term "distal" will refer to the end which is farther from the user.

Forceps 10 also includes an electrosurgical cable 310 which connects the forceps 10 to a source of electrosurgical energy, e.g., a generator (not shown). Generators such as those sold by Valleylab—a division of Tyco Healthcare LP, located in Boulder, Colo. are contemplated for use as a source of electrosurgical energy, e.g., FORCE EZ™ Electrosurgical Generator, FORCE FX™ Electrosurgical Generator, FORCE IC™, FORCE 2™ Generator, SurgiStat™ II. One such system is described in commonly-owned U.S. Pat. No. 6,033,399 entitled "ELECTROSURGICAL GENERATOR WITH ADAPTIVE POWER CONTROL," the entire contents of which are hereby incorporated by reference herein. Other systems have been described in commonly-owned U.S. Pat. No. 6,187,003 entitled "BIPOLAR ELECTROSURGICAL INSTRUMENT FOR SEALING VESSELS," the entire contents of which are also incorporated by reference herein.

In one embodiment, the generator includes various safety and performance features including isolated output, independent activation of accessories. In one embodiment, the electrosurgical generator includes Valleylab's Instant Response™ technology features which provide an advanced feedback system to sense changes in tissue 200 times per second and adjust voltage and current to maintain appropriate power. The Instant Response™ technology is believed to provide one or more of the following benefits to surgical procedure:

Consistent clinical effect through all tissue types;

Reduced thermal spread and risk of collateral tissue damage;

Less need to "turn up the generator"; and

Designed for the minimally invasive environment.

Cable 310 is internally divided into cable leads (not shown) which each transmit electrosurgical energy through their respective feed paths through the forceps 10 to the end effector assembly 100. A detailed discussion of the cable leads and their connections through the forceps 10 is described in commonly-assigned, co-pending U.S. application Ser. No. 10/460,926 entitled "VESSEL SEALER AND DIVIDER FOR USE WITH SMALL TROCARS AND CANNULAS" by Dycus et al., which is hereby incorporated by reference in its entirety herein.

Handle assembly 30 includes a fixed handle 50, a movable handle 40, a cutter lever 700 and a handle detent 710. Fixed handle 50 is integrally associated with housing 20 and movable handle 40 is movable relative to fixed handle 50 as explained in more detail below with respect to the operation of the forceps 10.

In one embodiment, rotating assembly 80 is integrally associated with the housing 20 and is rotatable approximately 180 degrees in either direction about a longitudinal axis "A" (FIGS. 1 and 3). Details of the rotating assembly 80 are described in more detail with respect to FIGS. 9 and 10.

Housing 20 may be formed from two housing halves (not shown) which each include a plurality of interfaces which are dimensioned to mechanically align and engage one another to form housing 20 and enclose the internal working components of forceps 10. A detailed discussion of the housing halves and how they mechanically engage with one another is described in commonly-assigned, co-pending U.S. application Ser. No. 10/460,926 entitled "VESSEL SEALER AND DIVIDER FOR USE WITH SMALL TROCARS AND CANNULAS" by Dycus et al., which is hereby incorporated by reference in its entirety herein.

It is envisioned that a plurality of additional interfaces (not shown) may be disposed at various points around the periphery of housing halves for ultrasonic welding purposes, e.g., energy direction/deflection points. It is also contemplated that housing halves (as well as the other components described below) may be assembled together in any fashion known in the art. For example, alignment pins, snap-like interfaces, tongue and groove interfaces, locking tabs, adhesive ports, etc. may all be utilized either alone or in combination for assembly purposes.

Rotating assembly 80 includes two halves 82a and 82b (see FIGS. 13 and 19) which, when assembled, form the rotating assembly 80 which, in turn, houses the drive assembly 150 and the knife assembly 140. Half 82b includes a series of detents/flanges 375a, 375b, 375c and 375d which are dimensioned to engage a pair of corresponding sockets or other mechanical interfaces (not shown) disposed within rotating half 82a. In one embodiment, movable handle 40 is of unitary construction and is operatively connected to the housing 20 and the fixed handle 50 during the assembly process.

As mentioned above, end effector assembly 100 is attached at the distal end 14 of shaft 12 and includes a pair of opposing jaw members 110 and 120. Movable handle 40 of handle assembly 30 is in mechanical cooperation with drive assembly 150 which, together, mechanically cooperate to impart movement of the jaw members 110 and 120 from an open position wherein the jaw members 110 and 120 are disposed in spaced relation relative to one another, to a clamping or closed position wherein the jaw members 110 and 120 cooperate to grasp tissue 420 (FIG. 29) therebetween.

It is envisioned that jaw members 110 and 120 of end effector assembly 100 may be curved (as illustrated in FIG. 3) in order to reach specific anatomical structures and promote more consistent seals for certain procedures. For example, it is contemplated that dimensioning the jaw members 110 and 120 at an angle of about 45 degrees to about 70 degrees is preferred for accessing and sealing specific anatomical structures relevant to prostatectomies and cystectomies, e.g., the dorsal vein complex and the lateral pedicles. Other angles may be preferred for different surgical procedures. Such an end effector assembly with curved jaw members is described in commonly-assigned, co-pending U.S. application Ser. No. 10/834,764 entitled "ELECTROSURGICAL INSTRUMENT WHICH REDUCES DAMAGE TO ADJACENT TISSUE," by Dycus et al., which is hereby incorporated by reference in its entirety herein.

It is envisioned that the forceps 10 may be designed such that it is fully or partially disposable depending upon a particular purpose or to achieve a particular result. For example, end effector assembly 100 may be selectively and releasably engageable with the distal end 16 of the shaft 12 and/or the proximal end 14 of shaft 12 may be selectively and releasably engageable with the housing 20 and the handle assembly 30. In either of these two instances, the forceps 10 would be considered "partially disposable" or "reposable," i.e., a new or different end effector assembly 100 (or end effector assembly 100 and shaft 12) selectively replaces the old end effector assembly 100 as needed. As can be appreciated, the presently disclosed electrical connections would have to be altered to modify the instrument to a reposable forceps.

Turning now to the more detailed features of the present disclosure, movable handle 40 includes a finger loop 41 which has an aperture 42 defined therethrough which enables a user to grasp and move the movable handle 40 relative to the fixed handle 50. FIGS. 1 and 2 illustrate a movable handle 40 with finger loop 41 designed to be grasped and moved by a thumb, while FIG. 3 illustrates a movable handle 40 with finger loop 41 designed to be grasped and moved by one or more fingers. Further, the movable handle 40 of FIGS. 1 and 2 is on the proximal side of fixed handle 50, while the movable handle 40 of FIG. 3 is on the distal side of fixed handle 50. Movable handle 40 may also include one or more ergonomically-enhanced gripping elements (not shown) disposed along the inner peripheral edge of aperture 42 or on fixed handle 50 which is designed to facilitate gripping of the handles 40 and 50 during activation. It is envisioned that the gripping element may include one or more protuberances, scallops and/or ribs to enhance gripping.

As best seen in FIGS. 1 and 2, movable handle 40 is selectively moveable about a pivot point 29 from a first position (FIG. 1) relative to fixed handle 50 to a second position (FIG. 2) in closer proximity to the fixed handle 50 which, as explained below, imparts movement of the jaw members 110 and 120 relative to one another. It is contemplated that there may be intermediate positions between those shown in FIGS. 1 and 2, e.g., discrete closure points which correspond to ratchet positions as discussed in more detail below. Additionally, continued movement of the moveable handle 40 towards the fixed handle 50 first engages switch 500, which causes the tissue to be sealed, and then engages knife assembly 140, which cuts the tissue. Operation of the forceps is discussed further below.

As best seen in FIGS. 1-3 and 26, the lower end of the movable handle 40 includes a flange 90. Flange 90 also includes an end 95 which rides within a predefined channel 52 (see FIG. 26) and mechanically engages with ramps 57 disposed within fixed handle 50. Additional features with respect to the end 95 are explained below in the detailed discussion of the operational features of the forceps 10.

Movable handle 40 is designed to provide a distinct mechanical advantage over conventional handle assemblies due to the position of the pivot point 29 relative to the longitudinal axis "A" of the shaft 12 and the disposition of the drive assembly 150 along longitudinal axis "A." In other words, it is envisioned that by positioning the pivot point 29 above the drive assembly 150, the user gains lever-like mechanical advantage to actuate the jaw members 110 and 120 enabling the user to close the jaw members 110 and 120 with lesser force while still generating the required forces necessary to affect a proper and effective tissue seal and to cut the tissue 420. It is also envisioned that the unilateral design of the end effector assembly 100 will also increase mechanical advantage as explained in more detail below.

As shown best in FIGS. 4-8, the end effector assembly 100 includes opposing jaw members 110 and 120 which cooperate to effectively grasp tissue 420 for sealing purposes. The end effector assembly 100 is designed as a unilateral assembly in this particular embodiment, i.e., jaw member 120 is fixed relative to the shaft 12 and jaw member 110 pivots about a pivot pin 103 to grasp tissue 420. A bilateral jaw assembly is also envisioned wherein both jaw members are movable.

Figure 8:
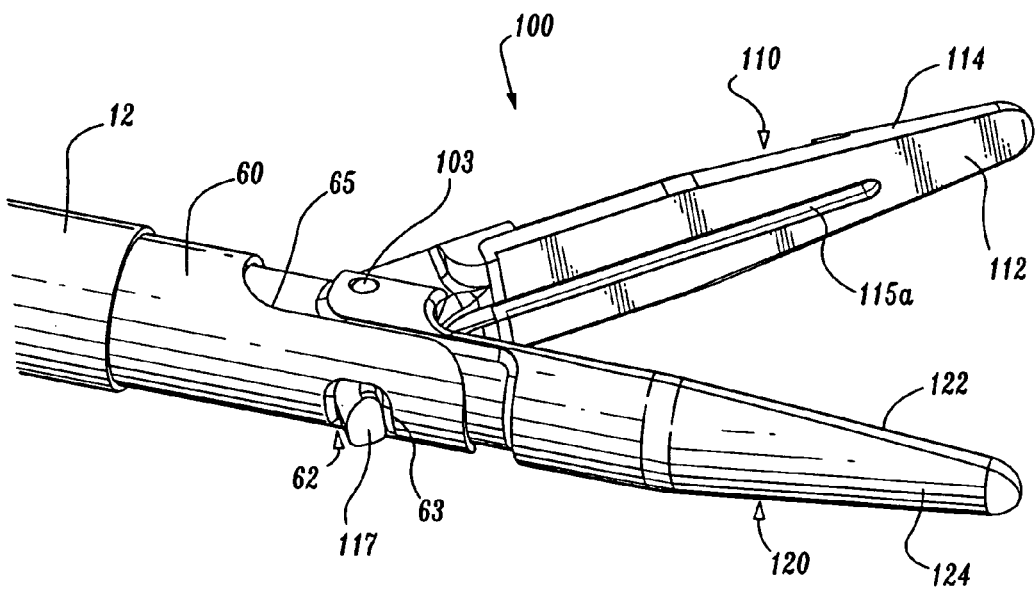
FIG. 8 is a full perspective view of the end effector assembly of FIG. 7.

More particularly, the unilateral end effector assembly 100 includes one stationary or fixed jaw member 120 mounted in fixed relation to the shaft 12 and pivoting jaw member 110 mounted about a pivot pin 103 attached to the stationary jaw member 120. A reciprocating sleeve 60 is slidingly disposed within the shaft 12 and is remotely operable by the drive assembly 150. The pivoting jaw member 110 includes a detent or protrusion 117 which extends from jaw member 110 through an aperture 62 disposed within the reciprocating sleeve 60 (FIG. 8). The pivoting jaw member 110 is actuated by sliding the sleeve 60 axially within the shaft 12 such that a distal end 63 of the aperture 62 abuts against the detent 117 on the pivoting jaw member 110 (see FIGS. 7 and 8). Pulling the sleeve 60 proximally closes the jaw members 110 and 120 about tissue 420 grasped therebetween and pushing the sleeve 60 distally opens the jaw members 110 and 120 for grasping purposes.

Figure 4:
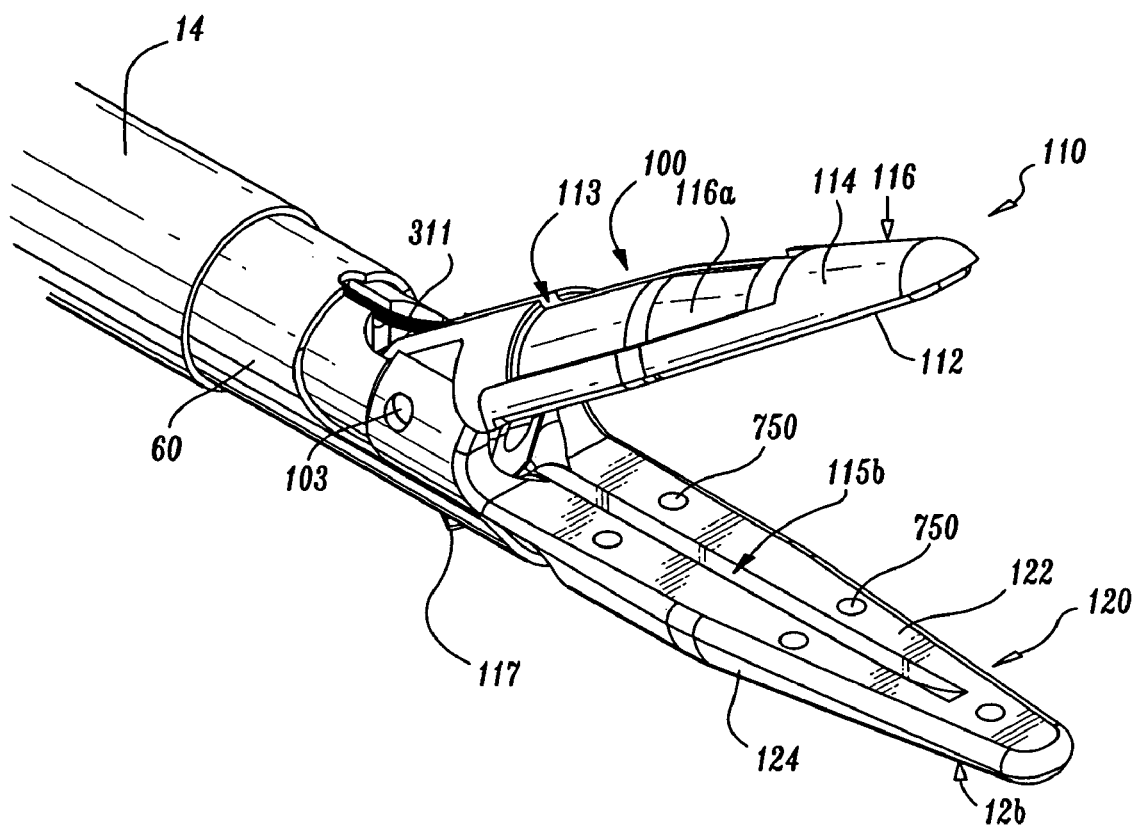
FIG. 4 is an enlarged, perspective view of an end effector assembly with jaw members shown in an open configuration.
Figure 5:
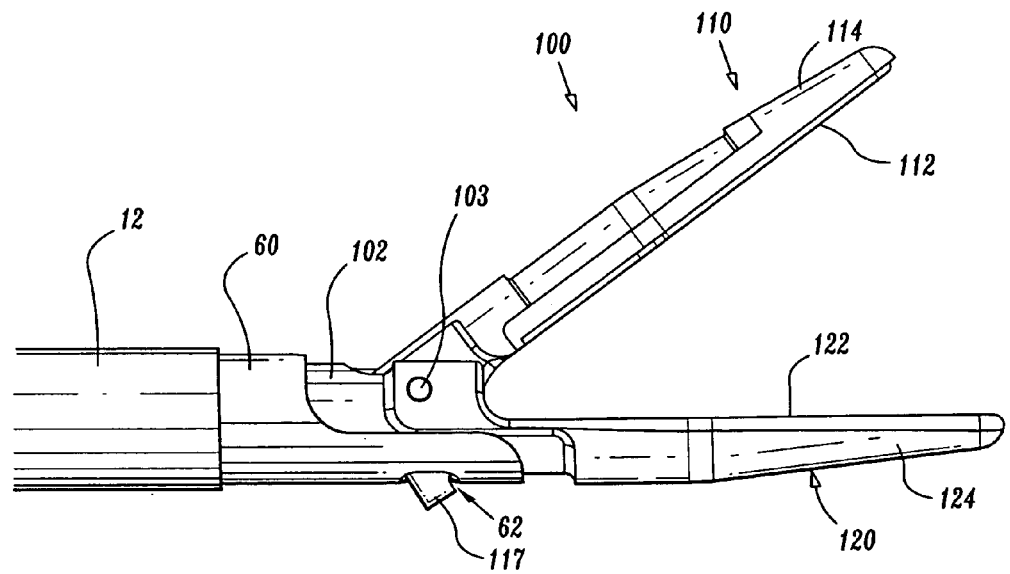
FIG. 5 is an enlarged, side view of the end effector assembly of FIG. 4.
Figure 6:
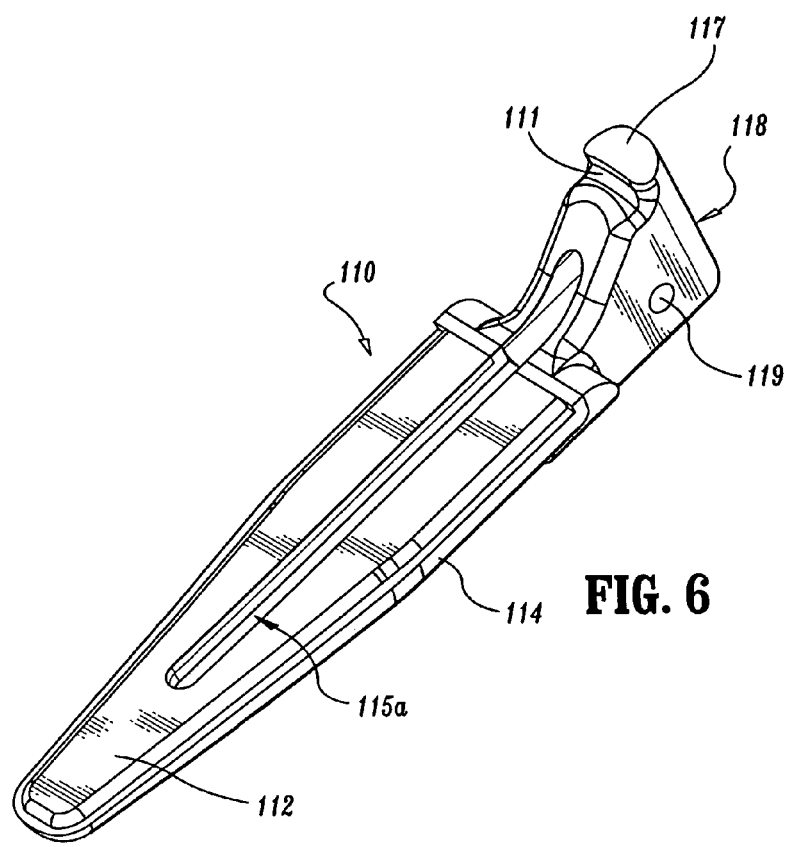
FIG. 6 is an enlarged, perspective view of the tissue contacting side of an upper jaw member of the end effector assembly.
Figure 7:
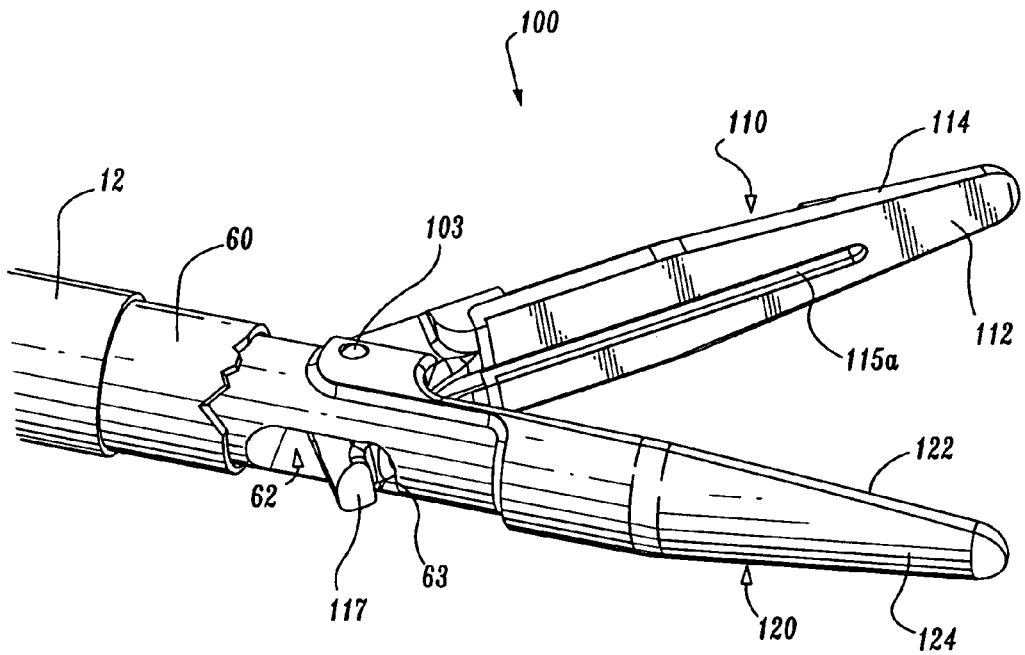
FIG. 7 is an enlarged, broken perspective view showing the end effector assembly and highlighting a cam-like closing mechanism which cooperates with a reciprocating pull sleeve to move the jaw members relative to one another.

As best illustrated in FIGS. 4 and 6, a knife channel 115a and 115b runs through the center of the jaw members 110 and 120, respectively, such that a knife blade 185 from the knife assembly 140 can cut the tissue 420 grasped between the jaw members 110 and 120 when the jaw members 110 and 120 are in a closed position. More particularly, the knife blade 185 can only be advanced through the tissue 420 when the jaw members 110 and 120 are closed thus preventing accidental or premature activation of the knife blade 185 through the tissue 420. Put simply, the knife channel 115 (made up of half channels 115a and 115b) is blocked when the jaws members 110 and 120 are opened and the knife channel 115 is aligned for distal activation when the jaw members 110 and 120 are closed (see FIGS. 25 and 27). It is also envisioned that the unilateral end effector assembly 100 may be structured such that electrical energy can be routed through the sleeve 60 at the protrusion 117 contact point with the sleeve 60 or using a "brush" or lever (not shown) to contact the back of the moving jaw member 110 when the jaw member 110 closes. In this instance, the electrical energy would be routed through the protrusion 117 to the stationary jaw member 120. Alternatively, a cable lead 311 may be routed to energize the stationary jaw member 120 and the other electrical potential may be conducted through the sleeve 60 and transferred to the pivoting jaw member 110 which establishes electrical continuity upon retraction of the sleeve 60. It is envisioned that this particular envisioned embodiment will provide at least two important safety features: 1) the knife blade 185 cannot extend while the jaw members 110 and 120 are opened; and 2) electrical continuity to the jaw members 110 and 120 is made only when the jaw members are closed. The illustrated forceps 10 only includes the knife channel 115.

As best shown in FIG. 4, jaw member 110 also includes a jaw housing 116 which has an insulative substrate or insulator 114 and an electrically conducive surface 112. In one embodiment, insulator 114 is dimensioned to securely engage the electrically conductive sealing surface 112. This may be accomplished by stamping, by overmolding, by overmolding a stamped electrically conductive sealing plate and/or by overmolding a metal injection molded seal plate. For example and as shown in FIG. 11, the electrically conductive sealing plate 112 includes a series of upwardly extending flanges 111a and 111b which are designed to matingly engage the insulator 114. The insulator 114 includes a shoe-like interface 107 disposed at a distal end thereof which is dimensioned to engage the jaw housing 116 in a slip-fit manner. The shoe-like interface 107 may also be overmolded about the outer periphery of the jaw 110 during a manufacturing step. It is envisioned that cable lead 311 terminates within the shoe-like interface 107 at the point where cable lead 311 electrically connects to the seal plate 112 (not shown). The movable jaw member 110 also includes a wire channel 113 which is designed to guide cable lead 311 into electrical continuity with sealing plate 112.

All of these manufacturing techniques produce jaw member 110 having an electrically conductive surface 112 which is substantially surrounded by an insulating substrate 114. In one embodiment, the insulator 114, electrically conductive sealing surface 112 and the outer, non-conductive jaw housing 116 are dimensioned to limit and/or reduce many of the known undesirable effects related to tissue sealing, e.g., flashover, thermal spread and stray current dissipation. Alternatively, it is also envisioned that the jaw members 110 and 120 may be manufactured from a ceramic-like material and the electrically conductive surface(s) 112 may be coated onto the ceramic-like jaw members 110 and 120.

Jaw member 110 includes a pivot flange 118 (FIG. 6) which includes a protrusion 117. Protrusion 117 extends from pivot flange 118 and includes an arcuately-shaped inner surface 111 dimensioned to matingly engage the aperture 62 of sleeve 60 upon retraction thereof. Pivot flange 118 also includes a pin slot 119 which is dimensioned to engage pivot pin 103 to allow jaw member 110 to rotate relative to jaw member 120 upon retraction of the reciprocating sleeve 60. As explained in more detail below, pivot pin 103 also mounts to the stationary jaw member 120 through a pair of apertures 101a and 101b disposed within a proximal portion of the jaw member 120.

It is envisioned that the electrically conductive sealing surface 112 may also include an outer peripheral edge which has a pre-defined radius and the insulator 114 meets the electrically conductive sealing surface 112 along an adjoining edge of the sealing surface 112 in a generally tangential position. In one embodiment, at the interface, the electrically conductive surface 112 is raised relative to the insulator 114. These and other envisioned embodiments are discussed in co-pending, commonly assigned Application Serial No. PCT/US01/11412 entitled "ELECTROSURGICAL INSTRUMENT WHICH REDUCES COLLATERAL DAMAGE TO ADJACENT TISSUE" by Johnson et al. and co-pending, commonly assigned Application Serial No. PCT/US01/11411 entitled "ELECTROSURGICAL INSTRUMENT WHICH IS DESIGNED TO REDUCE THE INCIDENCE OF FLASHOVER" by Johnson et al., both of which are hereby incorporated by reference in their entirety herein.

The electrosurgical seal and/or cut can be made utilizing various electrode assemblies on the jaw members, such that energy is applied to the tissue through sealing plates. This and other envisioned electrosurgical sealing and cutting techniques are discussed in co-pending, commonly assigned application Ser. No. 10/932,612 entitled "VESSEL SEALING INSTRUMENT WITH ELECTRICAL CUTTING MECHANISM" by Johnson et al., which is hereby incorporated by reference in its entirety herein.

Figure 30:
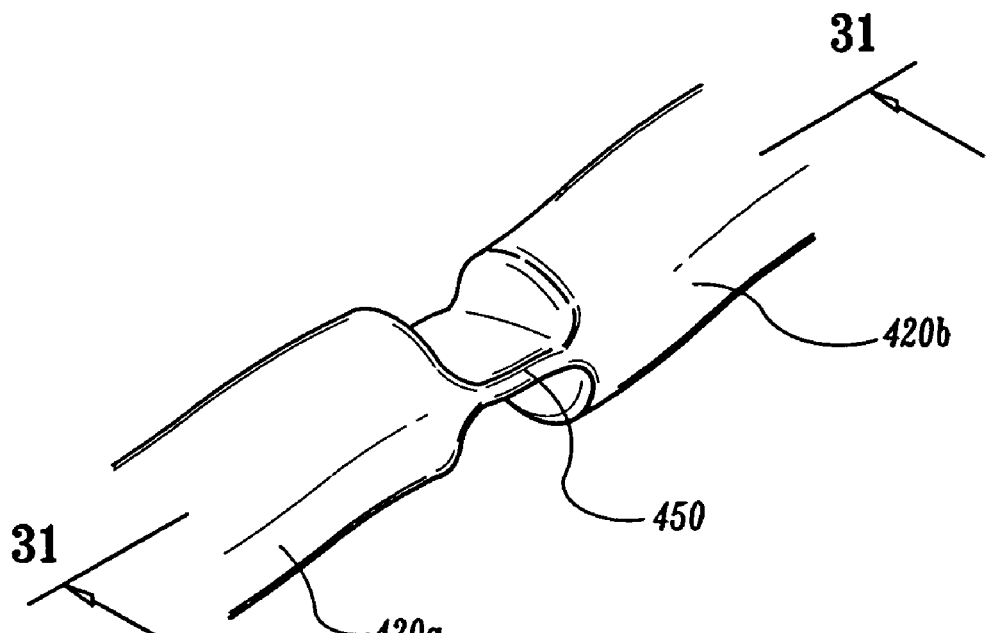
FIG. 30 is an enlarged view of a tissue seal.
Figure 31:
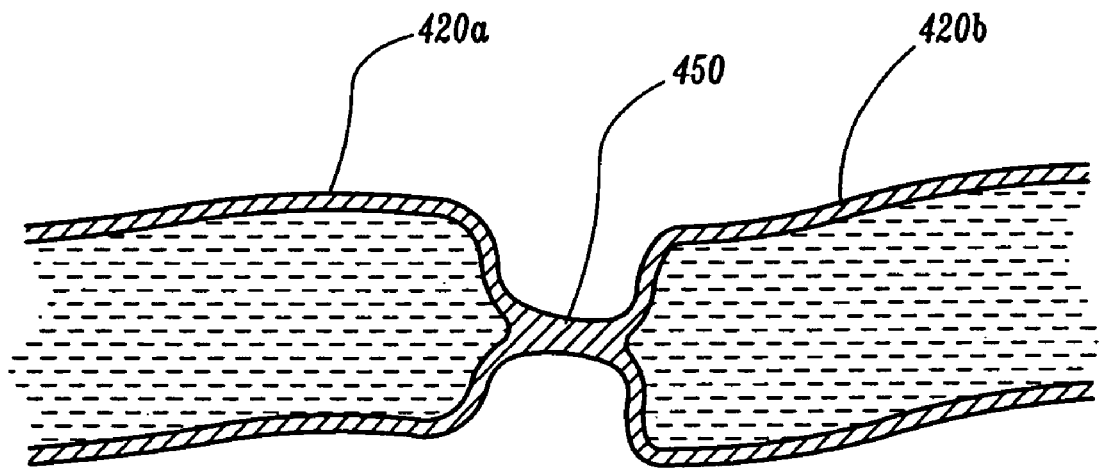
FIG. 31 is a side, cross section of a tissue seal taken along line 31-31 of FIG. 30.
Figure 32:
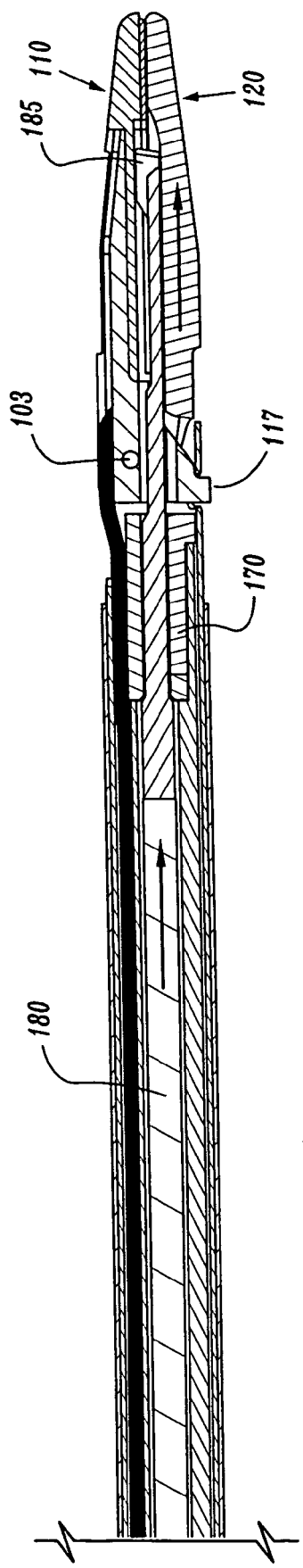
FIG. 32 is an enlarged view of the end effector showing distal translation of the knife.

In one embodiment, the electrically conductive surface 112 and the insulator 114, when assembled, form a longitudinally-oriented slot 115a defined therethrough for reciprocation of the knife blade 185. It is envisioned that the knife channel 115a cooperates with a corresponding knife channel 115b defined in stationary jaw member 120 to facilitate longitudinal extension of the knife blade 185 along a preferred cutting plane to effectively and accurately separate the tissue 420 along the formed tissue seal 450 (see FIGS. 30 and 33).

Jaw member 120 includes similar elements to jaw member 110 such as jaw housing 126 having an insulator 124 and an electrically conductive sealing surface 122 which is dimensioned to securely engage the insulator 124. Likewise, the electrically conductive surface 122 and the insulator 124, when assembled, include a longitudinally-oriented channel 115a defined therethrough for reciprocation of the knife blade 185. As mentioned above, when the jaw members 110 and 120 are closed about tissue 420, knife channels 115a and 115b form a complete knife channel 115 to allow longitudinal extension of the knife blade 185 in a distal fashion to sever tissue 420 along the tissue seal 450. It is also envisioned that the knife channel 115 may be completely disposed in one of the two jaw members, e.g., jaw member 120, depending upon a particular purpose. It is envisioned that the fixed jaw member 120 may be assembled in a similar manner as described above with respect to jaw member 110.

As best seen in FIG. 4, jaw member 120 includes a series of stop members 750 disposed on the inner facing surfaces of the electrically conductive sealing surface 122 to facilitate gripping and manipulation of tissue and to define a gap "G" (FIG. 29) between opposing jaw members 110 and 120 during sealing and cutting of tissue. It is envisioned that the series of stop members 750 may be employed on one or both jaw members 110 and 120 depending upon a particular purpose or to achieve a desired result. A detailed discussion of these and other envisioned stop members 750 as well as various manufacturing and assembling processes for attaching and/or affixing the stop members 750 to the electrically conductive sealing surfaces 112, 122 are described in commonly-assigned, co-pending U.S. Application Serial No. PCT/US01/11413 entitled "VESSEL SEALER AND DIVIDER WITH NON-CONDUCTIVE STOP MEMBERS" by Dycus et al. which is hereby incorporated by reference in its entirety herein.

Jaw member 120 is designed to be fixed to the end of a rotating tube 160 which is part of the rotating assembly 80 such that rotation of the tube 160 will impart rotation to the end effector assembly 100 (see FIGS. 13 and 19). Jaw member 120 includes a rear C-shaped cuff 170 having a slot 177 defined therein which is dimensioned to receive a slide pin 171. More particularly, slide pin 171 includes a slide rail 176 which extends substantially the length thereof which is dimensioned to slide into friction-fit engagement within slot 177. A pair of chamfered plates 172a and 172b extend generally radially from the slide rail 176 and include a radius which is substantially the same radius as the outer periphery of the rotating tube 160 such that the shaft 12 can encompass each of the same upon assembly.

As best shown in FIGS. 19 and 20, the rotating tube 160 includes an elongated guide slot 167 disposed in an upper portion thereof which is dimensioned to carry cable lead 311 therealong. The chamfered plates 172a and 172b also form a wire channel 175 which is dimensioned to guide the cable lead 311 from the tube 160 and into the movable jaw member 110 (see FIG. 4). Cable lead 311 carries a first electrical potential to movable jaw 110.

As shown in FIG. 19, the distal end of the tube 160 is generally C-shaped to include two upwardly extending flanges 162a and 162b which define a cavity 165 for receiving the proximal end of the fixed jaw member 120 inclusive of C-shaped cuff 170 and slide pin 171 (see FIG. 21). In one embodiment, the tube cavity 165 retains and secures the jaw member 120 in a friction-fit manner, however, the jaw member 120 may be welded to the tube 160 depending upon a particular purpose. Tube 160 also includes an inner cavity 169 defined therethrough which reciprocates the knife assembly 140 upon distal activation thereof and an elongated guide rail 163 which guides the knife assembly 140 during distal activation (see FIG. 20). The details with respect to the knife assembly are explained in more detail with respect to FIGS. 15-18. The proximal end of tube 160 includes a laterally oriented slot 168 which is designed to interface with the rotating assembly 80 as described below.

FIG. 19 also shows the rotating assembly 80 which includes C-shaped rotating halves 82a and 82b which, when assembled about tube 160, form a generally circular rotating member 82. More particularly, each rotating half, e.g., 82b, includes a series of mechanical interfaces 375a, 375b, 375c and 375d which matingly engage a corresponding series of mechanical interfaces in the other half, e.g., 82a, to form rotating member 82. Half 82b also includes a tab 89b which, together with a corresponding tab 89a disposed on half 82a (phantomly illustrated), cooperate to matingly engage slot 168 disposed on tube 160. As can be appreciated, this permits selective rotation of the tube 160 about axis "A" by manipulating the rotating member 82 in the direction of the arrow "B" (see FIG. 2).

As best shown in the exploded view of FIG. 11, jaw members 110 and 120 are pivotably mounted with respect to one another such that jaw member 110 pivots in a unilateral fashion from a first open position to a second closed position for grasping and manipulating tissue 420. More particularly, fixed jaw member 120 includes a pair of proximal, upwardly extending flanges 125a and 125b which define a cavity 121 dimensioned to receive flange 118 of movable jaw member 110 therein. As explained in detail below with respect to the operation of the jaw members 110 and 120, proximal movement of the tube 60 engages detent 117 to pivot the jaw member 110 to a closed position.

FIGS. 1-3 show the housing 20 and the component features thereof, namely, the handle assembly 30, the rotating assembly 80, the knife assembly 140, the drive assembly 150, the switch 500, the latch assembly 600 and a cutter lever 700.

The housing includes two halves (constructed similarly to the halves of rotating assembly 80, as discussed above with reference to FIG. 19) which, when mated, form housing 20. As can be appreciated, housing 20, once formed, houses the various assemblies identified above which will enable a user to selectively manipulate, grasp, seal and sever tissue 420 in a single action. In one embodiment, each half of the housing includes a series of mechanical interfacing components (not shown) which align and/or mate with a corresponding series of mechanical interfaces to align the two housing halves about the inner components and assemblies. The housing halves can then be sonic welded to secure the housing halves once assembled.

The movable handle 40 includes clevis 45 which pivots about pivot point 29 to pull the reciprocating sleeve 60 along longitudinal axis "A" and force a drive flange 47 against the drive assembly 150 which, in turn, closes the jaw members 110 and 120, as explained above. As mentioned above, the lower end of the movable handle 40 includes a flange 90 which has an end 95 which rides within a predefined channel 52 disposed within fixed handle 50 (see FIG. 26). The arrangement of the clevis 45 and the pivot point 29 of the movable handle 40 provides a distinct mechanical advantage over conventional handle assemblies due to the position of the pivot point 29 relative to the longitudinal axis "A" of the drive flange 47. In other words, by positioning the pivot point 29 above the drive flange 47, the user gains lever-like mechanical advantage to actuate the jaw members 110 and 120. This reduces the overall amount of mechanical force necessary to close the jaw members 110 and 120 to affect a tissue seal.

Movable handle 40 also includes a finger loop 41 which defines opening 42 which is dimensioned to facilitate grasping the movable handle 40. In one embodiment, finger loop 41 includes rubber insert which enhances the overall ergonomic "feel" of the movable handle 40.

Handle assembly 30 further includes a cutter lever 700 positioned within housing 20. When movable handle 40 is actuated (squeezed) past a certain threshold, a switch lever 502 is depressed by movable handle 40 to initiate a tissue seal cycle. A flexible detent 602 provides tactile feedback that the movable handle 40 is nearing an exit of the latch sealing zone and an end of the ramps 57. When the movable handle 40 is pushed past the flexible detent 602, end 95 of flange 90 drops down from ramps 57 and the user is able to return the movable handle 40 proximally to open the jaw members 110, 120 without cutting the seal. The user may also close the movable handle 40 to cut the sealed tissue 420 via actuation of the lever 700. When closing movable handle 40 farther to cut tissue, end 95 contacts a latch spring 704, which provides resistance on the movable handle 40. This provides an indication to the user that tissue cutting is about to begin.

The movable handle 40 or a handle detent 710 contacts the cutter lever 700, which activates knife assembly 140, which severs the tissue 420. As can be appreciated, this prevents accidental or premature severing of tissue 420 prior to completion of the tissue seal 450. The generator may provide an audible signal or other type of feedback when the seal cycle is complete. The surgeon can then safely cut the seal or return the movable handle 40 without cutting. In an alternative method, an electromechanical, mechanical or electrical feature could prevent cutting without initially sealing or without the surgeon activating a special over-ride feature.

Fixed handle 50 includes a channel 52 (FIG. 26) defined therein which is dimensioned to receive end 95 of flange 90 when movable handle 40 is actuated. The end 95 of flange 90 is dimensioned for facile reception with ramps 57 within channel 52 of fixed handle 50. It is envisioned that flange 90 may be dimensioned to allow a user to selectively, progressively and/or incrementally move jaw members 110 and 120 relative to one another from the open to closed positions. For example, it is contemplated that end 95 and ramps 57 may include a ratchet-like interface (FIGS. 1-3) which lockingly engages the movable handle 40 and, therefore, jaw members 110 and 120 at selective, incremental positions relative to one another depending upon a particular purpose. Such a ratchet-like interface can also prevent the movable handle 40 from becoming unactuated prior to the severing of tissue 420.

It is also contemplated that the ratchet-like interface between the end 95 and ramps 57 are configured such that a catch basin is disposed between each step of the ratchet. A catch basin is described in commonly-assigned, co-pending U.S. application Ser. No. 10/460,926 entitled "VESSEL SEALER AND DIVIDER FOR USE WITH SMALL TROCARS AND CANNULAS" by Dycus et al., which is hereby incorporated by reference in its entirety herein, and can be utilized to be a stopping point between each of the functions that the movable handle 40 can control (i.e., manipulation, clamping, sealing and cutting). Employing such a catch basin will enable the user to selectively advance the movable handle 40, while ensuring the functions are carried out in the proper order.

Other mechanisms may also be employed to control and/or limit the movement of movable handle 40 relative to fixed handle 50 (and jaw members 110 and 120) such as, e.g., hydraulic, semi-hydraulic, linear actuator(s), gas-assisted mechanisms and/or gearing systems.

In one embodiment, forceps 10 includes at least one tactile element which provides tactile feedback to the user to signify when tissue is being grasped, when the tissue has been sealed and/or when the tissue has been cut. Such a tactile element may include the turning on/off of lights (not shown) on housing 20 or mechanical vibrations being created in the fixed handle 50 or movable handle 40. It is further envisioned for a sensor to be disposed on or within forceps 10 to alert to the user when one or more completion stages has occurred, i.e., at the completion of tissue grasping, tissue sealing and/or tissue cutting.

Figure 26:
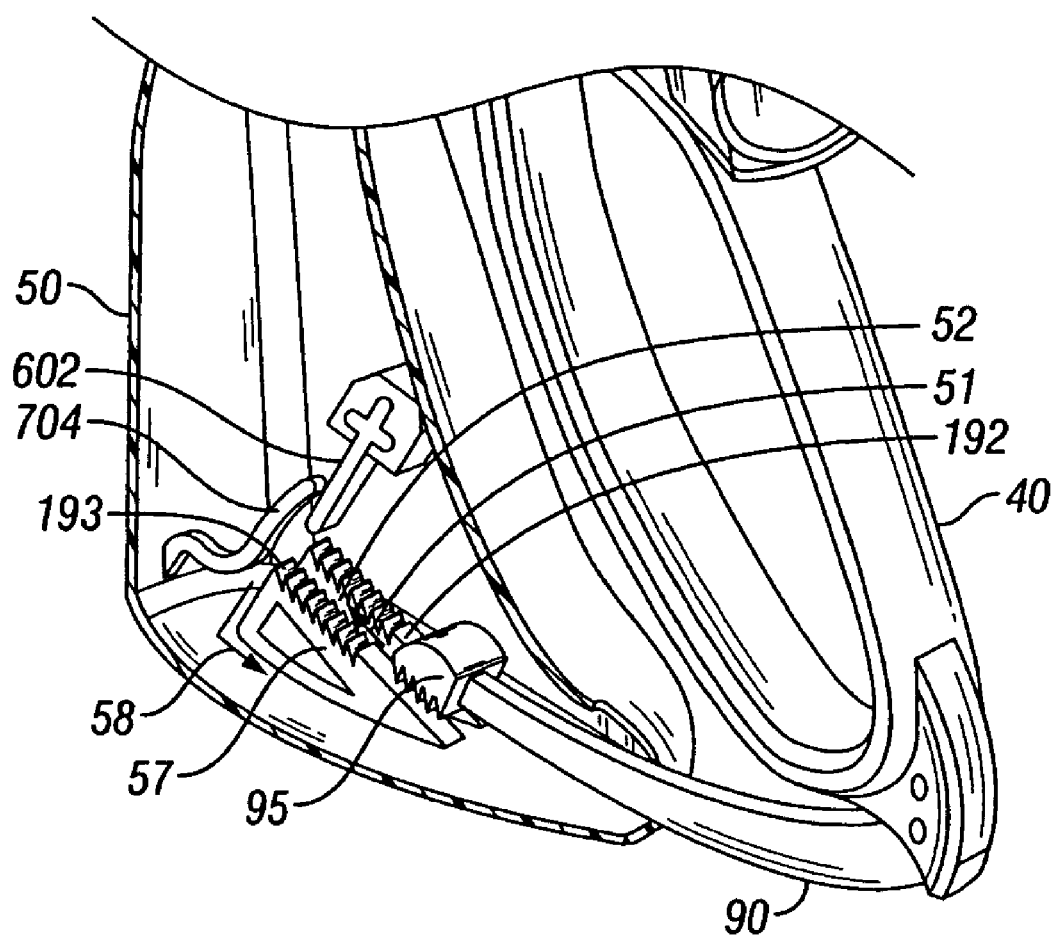
FIG. 26 is a greatly-enlarged, perspective view of a handle assembly and latch mechanism for use with the forceps.

As best illustrated in FIG. 26, housing halves form an internal cavity which predefines the channel 52 within fixed handle 50 such that an entrance pathway 51 and an exit pathway 58 are formed for reciprocation of the end 95 of flange 90 therein. When assembled, two ramps 57 are positioned to define a rail or track 192, such that the flange 90 can fit between the ramps 57 and end 95 moves along the track 192. During movement of end 95 of flange 90 along the entrance and exit pathways 51 and 58, respectively, the end 95 rides along track 192 according to the particular dimensions of the ramps 57, which, as can be appreciated, predetermines part of the overall pivoting motion of movable handle 40 relative to fixed handle 50.

As best illustrated in FIGS. 1 and 2, once actuated, movable handle 40 moves in a generally arcuate fashion towards fixed handle 50 about pivot point 29. End 95 of flange 90 moves along ramps 57 (shown as a single ramp in FIGS. 1-3 for clarity) which forces drive flange 47 against the drive assembly 150 which, in turn, pulls reciprocating sleeve 60 in a generally proximal direction to close jaw member 110 relative to jaw member 120. Continued actuation of movable handle 40 forces end 95 of flange 90 farther along ramps 57 and forces the movable handle 40 or cutter lever 700 into a contact 502 of switch 500, which causes the sealing of tissue 420 to occur. Continued actuation of movable handle 40 then forces movable handle detent 710 into cutter lever 700 to initiate engagement thereof. A detailed discussion of how the sealing occurs, including by electro-mechanical means, is described in commonly-assigned, co-pending U.S. application Ser. No. 10/932,612 entitled "VESSEL SEALING INSTRUMENT WITH ELECTRICAL CUTTING MECHANISM" by Johnson et al., which is hereby incorporated herein.

Continued actuation of movable handle 40 forces end 95 of flange 90 farther along the ramps 57 and into a flexible latch detent 602. The user feels a resistance when the end 95 contacts the flexible latch detent 602, which signifies that the device is about to exit the sealing position and either cut or return to its original position without cutting. To cut the tissue seal 450, the user continues to actuate the movable handle 40, such that the cutter lever 700 activates knife assembly 140, which in turn severs the tissue seal 450. At this cutting stage, the end 95 contacts a detent rib 704 which provides increased resistance to the user indicating that cutting of the tissue is about to begin. The end 95 slides distally along detent rib 704 (in the embodiment shown in FIG. 3, the detent rib 704 is contacted proximally). When the cut is complete, the detent rib 704 may stop the motion of the end 95 and allow flange 90 to follow its return path 58 (FIG. 26), as discussed above. Therefore, a full actuation of movable handle 40 grasps and clamps tissue 420, seals the tissue 420, and cuts the tissue seal 450, before returning the movable handle 40 to its original, unactuated position.

FIG. 3 illustrates the forceps 10 with the movable handle 40 located on the distal side of fixed handle 50. As can be appreciated, the internal dynamics of this embodiment are similar to those of the forceps illustrated in FIGS. 1 and 2, thus causing the forceps 10 to function in a comparable way.

It is envisioned that the flexible latch detent 602 may include one or more electro-mechanical switches, similar to those of switch 500, to seal the tissue 420. In this embodiment, handswitch 500 and contact 502 are not necessary. Details relating to the handswitch are discussed below.

It is also envisioned that latch spring 704 may include one or more mechanical or electro-mechanical switches or activations to drive the knife assembly 140 to cut the tissue seal 450, such that when end 95 contacts the latch spring 704, the tissue seal 450 is automatically severed.

The operating features and relative movements of the internal working components of the forceps 10 are shown as phantom lines in the various figures.

As the movable handle 40 is actuated and flange 90 is incorporated into channel 52 of fixed handle 50, the drive flange 47, through the mechanical advantage of the above-the-center pivot points, biases a ring flange 154 of drive ring 159 which, in turn, compresses a drive spring 67 against a rear ring 156 of the drive assembly 150 (FIG. 28). As a result thereof, the rear ring 156 reciprocates sleeve 60 proximally which, in turn, closes jaw member 110 onto jaw member 120. It is envisioned that the utilization of an over-the-center pivoting mechanism will enable the user to selectively compress the drive spring 67 a specific distance which, in turn, imparts a specific pulling load on the reciprocating sleeve 60 which is converted to a rotational torque about the jaw pivot pin 103. As a result, a specific closure force can be transmitted to the opposing jaw members 110 and 120.

FIG. 26 shows the initial actuation of movable handle 40 towards fixed handle 50 which causes the end 95 of flange 90 to move generally proximally and upwardly along entrance pathway 51 (this illustration is the embodiment of the forceps shown in FIG. 3; the internal environment of the forceps of FIGS. 1 and 2 is similarly situated). During movement of the flange 90 along the entrance and exit pathways 51 and 58, respectively, the end 95 rides along track 192 along the ramps 57. Once the tissue 420 is clamped, sealed and cut, end 95 clears edge 193 and movable handle 40 and flange 90 are redirected to exit pathway 58, where the movable handle 40 returns to its unactuated position.

As mentioned above, the jaw members 110 and 120 may be opened, closed and rotated to manipulate tissue 420 until sealing is desired. This enables the user to position and reposition the forceps 10 prior to activation and sealing. The end effector assembly 100 is rotatable about longitudinal axis "A" through rotation of the rotating assembly 80. It is envisioned that the feed path of the cable lead 311 through the rotating assembly 80, along shaft 12 and, ultimately, to the jaw member 110 enables the user to rotate the end effector assembly 100 approximately 180 degrees in both the clockwise and counterclockwise directions without tangling or causing undue strain on cable lead 311. As can be appreciated, this facilitates the grasping and manipulation of tissue 420.

Again as best shown in FIGS. 1 and 2, cutter lever 700 mounts adjacent movable handle 40 and cooperates with the knife assembly 140 to selectively translate knife blade 185 through a tissue seal 450.

Distal activation of the movable handle 40 (in the embodiment shown in FIGS. 1 and 2) forces the cutter lever 700 distally, which, as explained in more detail below, ultimately extends the knife blade 185 through the tissue 420. A knife spring 350 biases the knife assembly 70 in a retracted position such that after severing tissue 420 the knife blade 185 and the knife assembly 70 are automatically returned to a pre-firing position.

Drive assembly 150 includes reciprocating sleeve 60, drive housing 158, drive spring 67, drive ring 159, drive stop 155 and guide sleeve 157 which all cooperate to form the drive assembly 150. More particularly and as best shown in FIGS. 22 and 23, the reciprocating sleeve 60 includes a distal end 65 which as mentioned above has an aperture 62 formed therein for actuating the detent 117 of jaw member 110. In one embodiment, the distal end 65 includes a scoop-like support member 69 for supporting a proximal end 61 of the fixed jaw member 120 therein. The proximal end 61 of the reciprocating sleeve 60 includes a slot 68 defined therein which is dimensioned to slidingly support the knife assembly 70 for longitudinal reciprocation thereof to sever tissue 420. The slot 68 also permits retraction of the reciprocating sleeve 60 over the knife assembly 140 during the closing of jaw member 110 relative to jaw member 120.

The proximal end 61 of the reciprocating sleeve 60 is positioned within an aperture 151 in drive housing 158 to permit selective reciprocation thereof upon actuation of the movable handle 40. The drive spring 67 is assembled atop the drive housing 158 between a rear stop 156 of the drive housing 158 and a forward stop 154 of the drive ring 159 such that movement of the forward stop 154 compresses the drive spring 67 against the rear stop 156 which, in turn, reciprocates the drive sleeve 60. As a result thereof, the jaw members 110 and 120 and the movable handle 40 are biased by drive spring 67 in an open configuration. The drive stop 155 is fixedly positioned atop the drive housing 158 and biases the movable handle 40 when actuated such that the drive flange 47 forces the stop 154 of the drive ring 159 proximally against the force of the drive spring 67. The drive spring 67, in turn, forces the rear stop 156 proximally to reciprocate the sleeve 60. In one embodiment, the rotating assembly 80 is located proximal to the drive flange 47 to facilitate rotation of the end effector assembly 100. The guide sleeve 157 mates with the proximal end 61 of the reciprocating sleeve 60 and affixes to the drive housing 158. The assembled drive assembly 150 is shown best in FIG. 14.

As best shown in FIGS. 12 and 15-18, the knife assembly 140 includes an elongated rod 182 having a bifurcated distal end comprising prongs 182a and 182b which cooperate to receive a knife bar 184 therein. The knife assembly 180 also includes a proximal end 183 which is keyed to facilitate insertion into tube 160 of the rotating assembly 80. A knife wheel 148 is secured to the knife bar 182 by a pin 143. More particularly, the elongated knife rod 182 includes apertures 181a and 181b which are dimensioned to receive and secure the knife wheel 148 to the knife rod 182 such that longitudinal reciprocation of the knife wheel 148, in turn, moves the elongated knife rod 182 to sever tissue 420.

In one embodiment, the knife wheel 148 is donut-like and includes rings 141a and 141b which define a drive slot 147 designed to receive a drive bar (not shown) such that actuation of the movable handle 40 forces the drive bar and the knife wheel 148 distally. It is envisioned that apertures 181a and 181b may be used for different configurations. As such, pin 143 is designed for attachment through either aperture 181a or 181b to mount the knife wheel 148 (see FIG. 18). Knife wheel 148 also includes a series of radial flanges 142a and 142b which are dimensioned to slide along both channel 163 of tube 160 and slot 68 of the reciprocating sleeve 60 (see FIG. 9).

As mentioned above, the knife rod 182 is dimensioned to mount the knife bar 184 between prongs 182a and 182b, which can be in a friction-fit engagement. The knife bar 184 includes a series of steps 186a, 186b and 186c which reduce the profile of the knife bar 184 towards the distal end thereof. The distal end of the knife bar 184 includes a knife support 188 which is dimensioned to retain knife blade 185. The end of the knife support 188 can include a chamfered edge 188a. It is envisioned that the knife blade 185 may be welded to the knife support 188 or secured in any manner known in the trade.

As best shown in FIGS. 1 and 2, as the tissue is securely grasped and the cutter lever 700 advances distally due to actuation of movable handle 40, switch 500 activates, by virtue of movable handle 40 engaging contact 502. At this point, electrosurgical energy is transferred through cable leads to jaw members 110 and 120, as described in commonly-assigned, co-pending U.S. application Ser. No.

10/460,926 entitled "VESSEL SEALER AND DIVIDER FOR USE WITH SMALL TROCARS AND CANNULAS" by Dycus et al., which is hereby incorporated by reference in its entirety herein. As can be appreciated from the mechanics of the forceps 10, the switch 500 cannot fire unless the jaw members 110 and 120 are closed. A sensor (not shown) may be included in the generator or the housing which prevents activation unless the jaw members 110 and 120 have tissue 420 held therebetween. In addition, other sensor mechanisms may be employed which determine pre-surgical, concurrent surgical (i.e., during surgery) and/or post surgical conditions. The sensor mechanisms may also be utilized with a closed-loop feedback system coupled to the electrosurgical generator to regulate the electrosurgical energy based upon one or more pre-surgical, concurrent surgical or post surgical conditions. Various sensor mechanisms and feedback systems are described in commonly-owned, co-pending U.S. patent application Ser. No. 10/427,832 entitled "METHOD AND SYSTEM FOR CONTROLLING OUTPUT OF RF MEDICAL GENERATOR" filed on May 1, 2003 the entire contents of which are hereby incorporated by reference herein.

Figure 24:
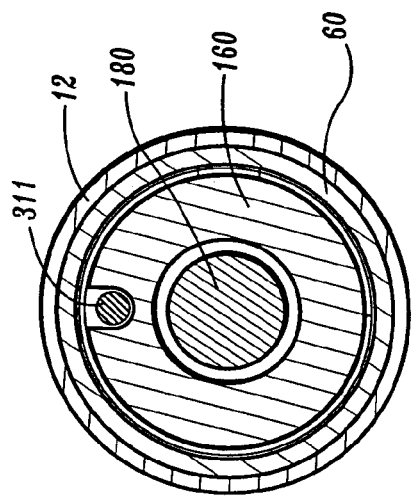
FIG. 24 is a greatly-enlarged, cross section of the shaft taken along line 24-24 of FIG. 25.
Figure 25:
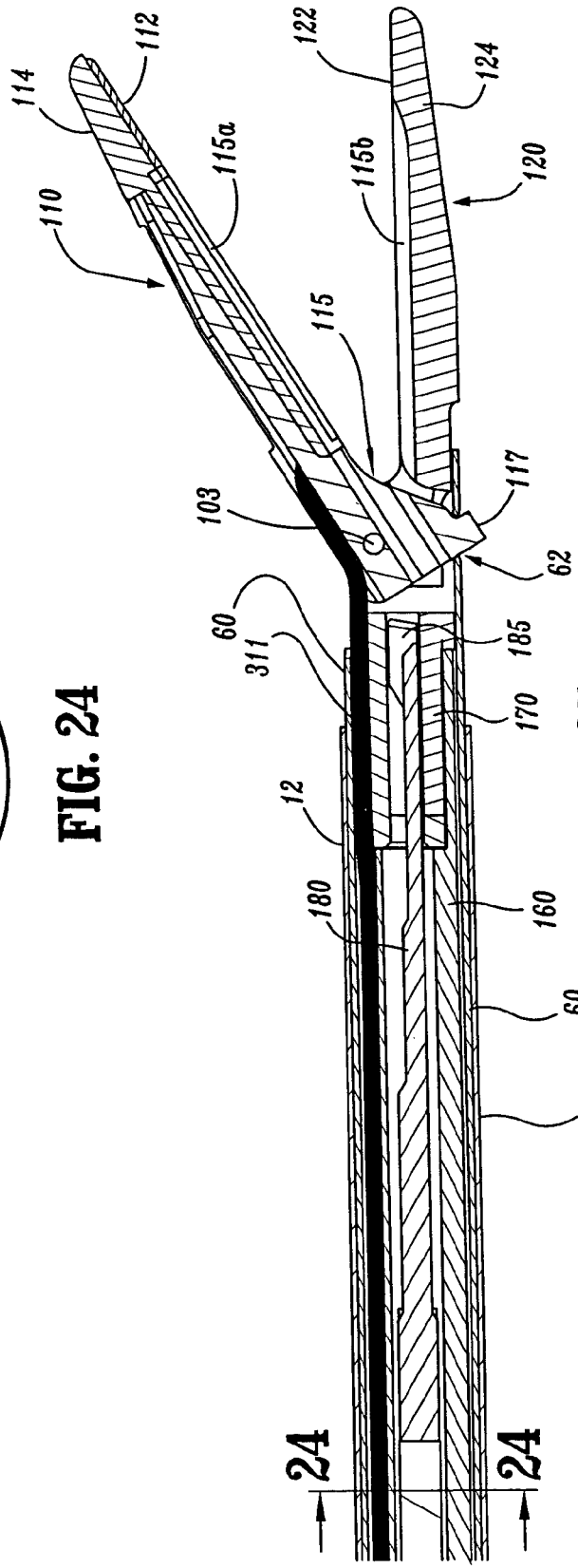
FIG. 25 is a side, cross section of the shaft and end effector assembly.

In one embodiment, the jaw members 110 and 120 are electrically isolated from one another such that electrosurgical energy can be effectively transferred through the tissue 420 to form seal 450. For example and as best illustrated in FIGS. 24 and 25, each jaw member, e.g., 110, includes a uniquely-designed electrosurgical cable path disposed therethrough which transmits electrosurgical energy to the electrically conductive sealing surface 112. It is envisioned that jaw member 110 may include one or more cable guides or crimp-like electrical connectors to direct cable lead 311 towards electrically conductive sealing surface 112. In one embodiment, cable lead 311 is held loosely but securely along the cable path to permit rotation of the jaw member 110 about pivot 103. As can be appreciated, this isolates electrically conductive sealing surface 112 from the remaining operative components of the end effector assembly 100, jaw member 120 and shaft 12. The second electrical potential is conducted to jaw member 120 through tube 160. The two potentials are isolated from one another by virtue of the insulative sheathing surrounding cable lead 311.

It is contemplated that utilizing a cable feed path for cable lead 311 and by utilizing a conductive tube 160 to carry the first and second electrical potentials not only electrically isolates each jaw member 110 and 120 but also allows the jaw members 110 and 120 to pivot about pivot pin 103 without unduly straining or possibly tangling cable lead 311. Moreover, it is envisioned that the simplicity of the electrical connections greatly facilitates the manufacturing and assembly process and assures a consistent and tight electrical connection for the transfer of energy through the tissue 420.

As discussed in commonly-assigned, co-pending U.S. application Ser. No. 10/460,926 entitled "VESSEL SEALER AND DIVIDER FOR USE WITH SMALL TROCARS AND CANNULAS" by Dycus et al., which is hereby incorporated by reference in its entirety herein, it is envisioned that select cable leads are fed through halves 82a and 82b of the rotating assembly 80 in such a manner to allow rotation of the shaft 12 (via rotation of the rotating assembly 80) in the clockwise or counter-clockwise direction without unduly tangling or twisting the cable leads. More particularly, select cable leads are fed through a series of conjoining slots 84a, 84b, 84c and 84d located in the two halves 82a and 82b of the rotating assembly 80. In one embodiment, each conjoining pair of slots, e.g., 84a, 84b and 84c, 84d, is large enough to permit rotation of the rotating assembly 80 without unduly straining or tangling the cable leads. The presently disclosed cable lead feed path is envisioned to allow rotation of the rotation assembly approximately 180 degrees in either direction.

Turning back to FIGS. 1-3 which show a view of the housing 20, rotating assembly 80, movable handle 40, fixed handle 50, latch assembly 600, switch 500 and cutter lever 700, it is envisioned that all of these various component parts along with the shaft 12 and the end effector assembly 100 are assembled during the manufacturing process to form a partially and/or fully disposable forceps 10. For example and as mentioned above, the shaft 12 and/or end effector assembly 100 may be disposable and, therefore, selectively/releasably engagable with the housing 20 and rotating assembly 80 to form a partially disposable forceps 10 and/or the entire forceps 10 may be disposable after use.

Once assembled, drive spring 67 is poised for compression atop drive housing 158 upon actuation of the movable handle 40. More particularly, movement of the movable handle 40 about pivot point 29 reciprocates the flange 90 into fixed handle 50 and forces drive flange 47 against flange 154 of drive ring 159 to compress drive spring 67 against the rear stop 156 to reciprocate the sleeve 60 (see FIG. 28).

The switch 500 is prevented from firing before the tissue 420 is clamped by jaw members 110 and 120. For the sealing to take place, the movable handle 40 should be actuated far enough to contact (or, alternatively, for the cutter lever 700 to contact) the switch 500, contact 502 or a sensor (not shown). Before the switch 500 is contacted, the movable handle 40 should travel sufficiently far enough to cause jaw members 110 and 120 to be clamped. It is envisioned that the opposing jaw members 110 and 120 may be rotated and partially opened and closed before activation of switch 500 which, as can be appreciated, allows the user to grip and manipulate the tissue 420 before the tissue 420 is sealed.

It is envisioned that configuring the pivot 29 above or relative to a longitudinal axis defined through the shaft provides an increased mechanical advantage, thus facilitating and easing selective compression of the drive spring 67 a specific distance which, in turn, imparts a specific load on the reciprocating sleeve 60. As best seen in FIG. 2, the moveable handle 40 includes a drive cam surface 49' which is designed in-line with the longitudinal axis "A," which together with the position of the pivot 28 being disposed above axis "A," increase the mechanical advantage of the movable handle 40 and reduce the amount of force necessary to actuate the jaw members 110, 120 with the preferred closure force. The load of the reciprocating sleeve 60 is converted to a torque about the jaw pivot 103. As a result, a specific closure force can be transmitted to the opposing jaw members 110 and 120 between the range of about 3 kg/cm$^2$ to about 16 kg/cm$^2$. As mentioned above, the jaw members 110 and 120 may be opened, closed and rotated to manipulate tissue 420 until sealing is desired. This enables the user to position and re-position the forceps 10 prior to activation and sealing.

Once the desired position for the sealing site is determined and the jaw members 110 and 120 are properly positioned, movable handle 40 may be actuated farther such that the switch 500 is engaged to seal the tissue 420 with electrosurgical energy. Continued actuation of movable handle 40 engages knife assembly 140 (as discussed above), which causes the tissue seal 450 to be severed.

It is envisioned that the end effector assembly 100 and/or the jaw members 110 and 120 may be dimensioned to off-load some of the excessive clamping forces to prevent mechanical failure of certain internal operating elements of the end effector 100.

As can be appreciated, the combination of the increased mechanical advantage provided by the above-the-axis pivot 29 along with the compressive force associated with the drive spring 67 facilitate and assure consistent, uniform and accurate closure pressure about the tissue 420 within the desired working pressure range of about 3 kg/cm$^2$ to about 16 kg/cm$^2$ and, preferably, about 7 kg/cm$^2$ to about 13 kg/cm$^2$. By controlling the intensity, frequency and duration of the electrosurgical energy applied to the tissue 420, the user can effectively seal tissue.

In one embodiment, the electrically conductive sealing surfaces 112 and 122 of the jaw members 110 and 120, respectively, are relatively flat to avoid current concentrations at sharp edges and to avoid arcing between high points. In addition and due to the reaction force of the tissue 420 when engaged, jaw members 110 and 120 can be manufactured to resist bending. For example, the jaw members 110 and 120 may be tapered along the width thereof which is advantageous for two reasons: 1) the taper will apply constant pressure for a constant tissue thickness at parallel; 2) the thicker proximal portion of the jaw members 110 and 120 will resist bending due to the reaction force of the tissue 420.

As mentioned above, at least one jaw member, e.g., 120, may include a stop member 750 which limits the movement of the two opposing jaw members 110 and 120 relative to one another. In one embodiment, the stop member 750 extends a predetermined distance from the sealing surface 122 (according to the specific material properties [e.g., compressive strength, thermal expansion, etc.]) to yield a consistent and accurate gap distance "G" during sealing (FIG. 29). The gap distance between opposing sealing surfaces 112 and 122 during sealing ranges from about 0.001 inches to about 0.006 inches and, desirably, between about 0.002 and about 0.003 inches. It is envisioned that the non-conductive stop members 750 may be molded onto the jaw members 110 and 120 (e.g., overmolding, injection molding, etc.), stamped onto the jaw members 110 and 120 or deposited (e.g., deposition) onto the jaw members 110 and 120. For example, one technique involves thermally spraying a ceramic material onto the surface of the jaw member 110 and 120 to form the stop members 750. Several thermal spraying techniques are contemplated which involve depositing a broad range of heat resistant and insulative materials on various surfaces to create stop members 750 for controlling the gap distance between electrically conductive surfaces 112 and 122.

As energy is being selectively transferred to the end effector assembly 100, across the jaw members 110 and 120 and through the tissue 420, a tissue seal 450 forms isolating two tissue halves 420a and 420b. With other known vessel sealing instruments, the user then removes and replaces the forceps 10 with a cutting instrument (not shown) or manually activates another switch to divide the tissue halves 420a and 420b along the tissue seal 450. As can be appreciated, this is both time consuming and tedious and may result in inaccurate tissue division across the tissue seal 450 due to misalignment or misplacement of the cutting instrument along the ideal tissue cutting plane.

Figure 33:
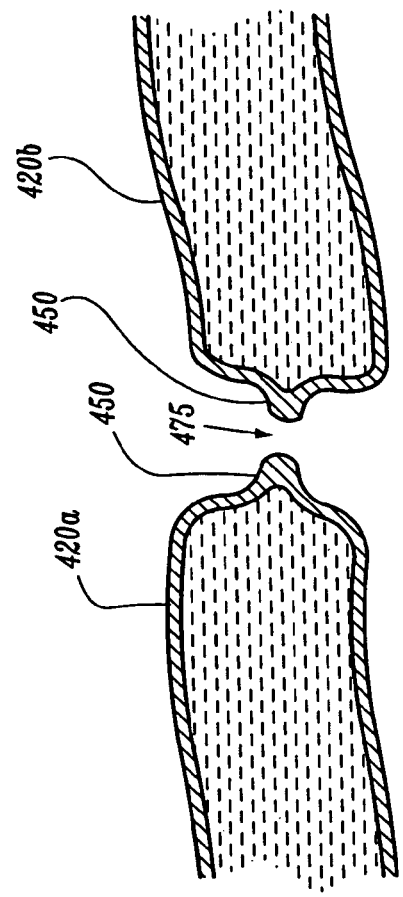
FIG. 33 is a side, cross section of a tissue seal after separation by the knife assembly.

As explained in detail above, the present disclosure incorporates a knife assembly 140 which, when activated via the handle assembly 30, progressively and selectively divides the tissue 420 along an ideal tissue plane in precise manner to effectively and reliably divide the tissue 420 into two sealed halves 420a and 420b with a tissue gap 475 therebetween (see FIG. 33). The knife assembly 140 in conjunction with the handle assembly 30 allows the user to quickly separate the tissue 420 immediately after sealing without substituting a cutting instrument through a cannula or trocar port and without having to perform a different action (e.g., manually activating a switch or pulling a trigger). As can be appreciated, accurate sealing and dividing of tissue 420 is accomplished with a single, continuous motion using the same forceps 10.

It is envisioned that knife blade 185 may also be coupled to the same or an alternative electrosurgical energy source to facilitate separation of the tissue 420 along the tissue seal 450 (not shown). Moreover, it is envisioned that the angle of the tip of the knife blade 185 may be dimensioned to provide more or less aggressive cutting angles depending upon a particular purpose. For example, the knife blade 185 may be positioned at an angle which reduces "tissue wisps" associated with cutting. Moreover, the knife blade 185 may be designed having different blade geometries such as serrated, notched, perforated, hollow, concave, convex etc. depending upon a particular purpose or to achieve a particular result.

From the foregoing and with reference to the various figure drawings, those skilled in the art will appreciate that certain modifications can also be made to the present disclosure without departing from the scope of the same. For example, it may be preferable to add other features to the forceps 10, e.g., an articulating assembly to axially displace the end effector assembly 100 relative to the elongated shaft 12.

It is also contemplated that the forceps 10 (and/or the electrosurgical generator used in connection with the forceps 10) may include a sensor or feedback mechanism (not shown) which automatically selects the appropriate amount of electrosurgical energy to effectively seal the particularly-sized tissue grasped between the jaw members 110 and 120. The sensor or feedback mechanism may also measure the impedance across the tissue during sealing and provide an indicator (visual and/or audible) that an effective seal has been created between the jaw members 110 and 120. Examples of such sensor systems are described in commonly-owned U.S. patent application Ser. No. 10/427,832 entitled "METHOD AND SYSTEM FOR CONTROLLING OUTPUT OF RF MEDICAL GENERATOR," filed on May 1, 2003 the entire contents of which are hereby incorporated by reference herein.

Although the figures depict the forceps 10 manipulating an isolated vessel 420, it is contemplated that the forceps 10 may be used with non-isolated vessels as well. Other cutting mechanisms are also contemplated to cut tissue 420 along the ideal tissue plane.

It is envisioned that the outer surface of the end effector assembly 100 may include a nickel-based material, coating, stamping, metal injection molding which is designed to reduce adhesion between the jaw members 110 and 120 with the surrounding tissue during activation and sealing. Moreover, it is also contemplated that the conductive surfaces 112 and 122 of the jaw members 110 and 120 may be manufactured from one (or a combination of one or more) of the following materials: nickel-chrome, chromium nitride, Med-Coat 2000 manufactured by The Electrolizing Corporation of OHIO, inconel 600 and tin-nickel. The tissue conductive surfaces 112 and 122 may also be coated with one or more of the above materials to achieve the same result, i.e., a "non-stick surface." As can be appreciated, reducing the amount that the tissue "sticks" during sealing improves the overall efficacy of the instrument.

One particular class of materials disclosed herein has demonstrated superior non-stick properties and, in some instances, superior seal quality. For example, nitride coatings which include, but not are not limited to: TiN, ZrN, TiAlN, and CrN are preferred materials used for non-stick purposes. CrN has been found to be particularly useful for non-stick purposes due to its overall surface properties and optimal performance. Other classes of materials have also been found to reducing overall sticking. For example, high nickel/chrome alloys with a Ni/Cr ratio of approximately 5:1 have been found to significantly reduce sticking in bipolar instrumentation. One particularly useful non-stick material in this class is Inconel 600. Bipolar instrumentation having sealing surfaces 112 and 122 made from or coated with Ni200, Ni201 (~100% Ni) also showed improved non-stick performance over typical bipolar stainless steel electrodes.

While several embodiments of the disclosure have been shown in the figures, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. An endoscopic bipolar forceps, comprising:
   a housing;
   a shaft affixed to the housing, the shaft having a longitudinal axis defined therethrough and an end effector assembly engaged at a distal end thereof, the end effector assembly including two jaw members moveable from a first position in spaced relation relative to one another to at least a second position closer to one another for grasping tissue therebetween, each of the jaw members adapted to connect to an electrosurgical energy source such that the jaw members are capable of conducting energy through tissue held therebetween to affect a tissue seal;
   a drive assembly disposed within the housing for moving the jaw members from the first position to the second position;
   a switch disposed within the housing which activates the electrosurgical energy source;
   a knife assembly which is advanceable to cut tissue disposed between the jaw members;
   a movable handle connected to the housing and selectively rotatable about a pivot, the pivot located a fixed distance above the longitudinal axis, wherein continual actuation of the movable handle initially engages the drive assembly to move the jaw members, subsequently engages the switch to activate the electrosurgical energy source to seal the tissue, and subsequently advances the knife assembly to cut tissue disposed between the jaw members.

2. An endoscopic bipolar forceps according to claim 1 further comprising a rotating assembly which rotates the jaw members about the longitudinal axis defined through the shaft.

3. An endoscopic bipolar forceps according to claim 1 wherein at least one of the jaw members includes at least one stop member disposed thereon which regulates the distance between the jaw members.

4. An endoscopic bipolar forceps according to claim 3 wherein the distance between the jaw members is between 0.001 inches and 0.006 inches.

5. An endoscopic bipolar forceps according to claim 1 wherein a pressure range for actuating the movable handle and creating an effective seal is between 3 kg/cm$^2$ to 16 kg/cm$^2$.

6. An endoscopic bipolar forceps according to claim 1 further including at least one tactile element which provides tactile feedback to a user relating to at least one of tissue sealing and tissue cutting.

7. An endoscopic bipolar forceps according to claim 1 further comprising a ratchet latch assembly associated with the movable handle and the housing such that the movable handle locks into a first ratchet position after it cooperates to manipulate tissue, and the movable handle locks into a second ratchet position after it cooperates to seal tissue.

8. A method for using an endoscopic bipolar forceps to grasp, seal and cut tissue, the method comprising the steps of:
   providing an endoscopic bipolar forceps, the forceps having a housing, a shaft affixed to the housing, the shaft having a longitudinal axis defined therethrough and an end effector assembly engaged at a distal end thereof, the end effector assembly including two jaw members moveable from a first position in spaced relation relative to one another to at least a second position closer to one another for grasping tissue therebetween, each of the jaw members adapted to connect to an electrosurgical energy source such that the jaw members are capable of conducting energy through tissue held therebetween to affect a tissue seal, a drive assembly disposed within the housing for moving the jaw members from the first position to the second position, a switch disposed within the housing which activates the electrosurgical energy source, a knife assembly which is advanceable to cut tissue disposed between the jaw members, and a movable handle connected to the housing and selectively rotatable about a pivot, the pivot located a fixed distance above the longitudinal axis, wherein continual actuation of the movable handle initially engages the drive assembly to move the jaw members, subsequently engages the switch to activate the electrosurgical energy source to seal the tissue, and subsequently advances the knife assembly to cut tissue disposed between the jaw members;
   actuating the movable handle, a continued actuation of the movable handle engages the drive assembly and moves the jaw members relative to one another to grasp tissue, engages the switch and activates the electrosurgical energy to seal tissue, and advances the knife assembly to cut the tissue.

9. An surgical instrument for surgically joining tissue, the surgical instrument comprising:
   a handle assembly;
   a shaft extending distally from the handle assembly and defining a longitudinal axis therethrough;
   an end effector assembly disposed at a distal end of the shaft, the end effector assembly including two jaw members moveable from a first position in spaced relation relative to one another to at least a second position closer to one another for grasping tissue therebetween;
   a drive assembly disposed in mechanical cooperation with the handle assembly for moving the jaw members between the first position and the second position;
   a knife assembly configured to cut tissue disposed between the jaw members;
   a tactile element configured to provide feedback to the user after tissue has been joined;
   a movable handle disposed in mechanical cooperation with the handle assembly, wherein the movable handle is movable from a first, non-actuated position to a second position where the movable handle engages the drive assembly to move at least one of the jaw members, wherein the movable handle is movable between the second position and a third position to cause tissue to be joined, wherein the movable handle engages the tactile element when the movable handle reaches the third position, wherein the movable handle is movable between the third position and a fourth position where the movable handle engages the knife assembly to cut tissue, and wherein the movable handle is movable between the third position and the first, non-actuated position without the movable handle moving towards the fourth position.

10. The surgical instrument of claim 9, wherein each of the jaw members is adapted to connect to an electrosurgical energy source such that the jaw members are capable of conducting energy through tissue held therebetween to affect a tissue seal.

11. The surgical instrument of claim 10, further comprising a switch disposed within the handle assembly that activates the electrosurgical energy source.

12. The surgical instrument of claim 9, further comprising a second tactile element, the second tactile element being configured to provide feedback to the user while tissue is being cut.

13. The surgical instrument of claim 12, wherein the second tactile element is disposed within the handle assembly.

14. The surgical instrument of claim 9, wherein the tactile element is disposed within the handle assembly.

* * * * *